US012070538B2

(12) United States Patent
Crnkovich et al.

(10) Patent No.: US 12,070,538 B2
(45) Date of Patent: Aug. 27, 2024

(54) DRAIN APPARATUS FOR HEMODIALYSIS MACHINES

(71) Applicant: Fresenius Medical Care Holdings, Inc., Waltham, MA (US)

(72) Inventors: Martin Joseph Crnkovich, Walnut Creek, CA (US); Colin Weaver, Pleasanton, CA (US); David Yuds, Hudson, NH (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 18/160,383

(22) Filed: Jan. 27, 2023

(65) Prior Publication Data

US 2023/0166015 A1    Jun. 1, 2023

Related U.S. Application Data

(62) Division of application No. 16/588,151, filed on Sep. 30, 2019, now Pat. No. 11,596,721.

(51) Int. Cl.
*A61M 1/16* (2006.01)
*A61M 1/26* (2006.01)
(Continued)

(52) U.S. Cl.
CPC ........ *A61M 1/1621* (2014.02); *A61M 1/1601* (2014.02); *A61M 1/1637* (2014.02);
(Continued)

(58) Field of Classification Search
CPC .............. A61M 1/1601; A61M 1/1621; A61M 1/1637; A61M 1/165; A61M 1/1686;
(Continued)

(56) References Cited

U.S. PATENT DOCUMENTS

| 3,441,136 A | 4/1969 | Serfass et al. |
| 3,871,913 A | 3/1975 | Shaldon |
| 2011/0163030 A1 | 7/2011 | Weaver et al. |

FOREIGN PATENT DOCUMENTS

| JP | 2014-050509 | 3/2014 |
| WO | WO 2005/118485 | 12/2005 |

OTHER PUBLICATIONS

International Preliminary Report on Patentability in International Appln. No. PCT/US2020/053235, mailed Apr. 14, 2022, 14 pages.
(Continued)

*Primary Examiner* — Dirk R Bass
(74) *Attorney, Agent, or Firm* — Fish & Richardson P.C.

(57) ABSTRACT

This disclosure relates to dialysis systems and methods. In some implementations, a dialysis system includes a dialysis machine with a fluid line and a drain line, a blood line set configured to be connected to the dialysis machine, and a drain apparatus coupled to the dialysis machine. The drain apparatus includes a chamber configured to receive an end of a patient line of the blood line set, an inlet line, an outlet line, and a valve. The inlet line has a first end configured to be coupled to the chamber and a second end configured to be coupled to the fluid line of the dialysis machine. The outlet line has a first end configured to be coupled to the chamber and a second end configured to be coupled to the drain line of the dialysis machine. The valve is configured to control flow of fluid through the outlet line.

10 Claims, 18 Drawing Sheets

(51) Int. Cl.
  *A61M 1/34* (2006.01)
  *A61M 1/36* (2006.01)
(52) U.S. Cl.
  CPC .......... *A61M 1/1686* (2013.01); *A61M 1/169* (2013.01); *A61M 1/267* (2014.02); *A61M 1/3413* (2013.01); *A61M 1/36225* (2022.05); *A61M 1/3626* (2013.01); *A61M 1/3627* (2013.01); *A61M 2205/18* (2013.01); *A61M 2205/3306* (2013.01); *A61M 2205/3341* (2013.01); *A61M 2205/3368* (2013.01); *A61M 2205/3375* (2013.01); *A61M 2205/3389* (2013.01); *A61M 2205/505* (2013.01); *A61M 2205/581* (2013.01); *A61M 2205/7536* (2013.01)
(58) Field of Classification Search
  CPC .... A61M 1/1688; A61M 1/169; A61M 1/267; A61M 1/3413; A61M 1/3624; A61M 1/3626; A61M 1/3627; A61M 1/3644; A61M 1/3646; A61M 1/367; A61M 2205/18; A61M 2205/3306; A61M 2205/3341; A61M 2205/3368; A61M 2205/3375; A61M 2205/3389; A61M 2205/505; A61M 2205/581; A61M 2205/7536
  See application file for complete search history.

(56) References Cited

OTHER PUBLICATIONS

International Search Report and Written Opinion in International Appln. No. PCT/US2020/053235, mailed Jan. 14, 2021, 20 pages.

DRAIN APPARATUS FOR HEMODIALYSIS MACHINES

CROSS-REFERENCE TO RELATED APPLICATIONS

This application is a divisional application of and claims the benefit of priority under 35 U.S.C. § 121 to U.S. application Ser. No. 16/588,151, filed on Sep. 30, 2019, the contents of which are hereby incorporated by reference.

TECHNICAL FIELD

This disclosure relates to dialysis systems and methods.

BACKGROUND

Dialysis is a treatment used to support a patient with insufficient renal function. The two principal dialysis methods are hemodialysis and peritoneal dialysis.

During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), a patient's peritoneal cavity is periodically infused with dialysis solution or dialysate. The membranous lining of the patient's peritoneum acts as a natural semi-permeable membrane that allows diffusion and osmosis exchanges to take place between the solution and the blood stream. These exchanges across the patient's peritoneum, like the continuous exchange across the dialyzer in HD, result in the removal of waste products, including solutes like urea and creatinine, from the blood, and regulate the levels of other substances, such as sodium and water, in the blood.

Many PD machines are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle.

SUMMARY

In one aspect, a dialysis system includes a dialysis machine with a fluid line and a drain line, a blood line set configured to be connected to the dialysis machine, and a drain apparatus coupled to the dialysis machine. The drain apparatus includes a chamber configured to receive an end of a patient line of the blood line set, an inlet line, an outlet line, and a valve. The inlet line has a first end configured to be coupled to the chamber and a second end configured to be coupled to the fluid line of the dialysis machine. The outlet line has a first end configured to be coupled to the chamber and a second end configured to be coupled to the drain line of the dialysis machine. The valve is coupled to the outlet line and configured to control flow of fluid through the outlet line.

In another aspect, a drain apparatus for a dialysis machine includes a chamber, a lid, an inlet line, an outlet line, and a valve. The chamber is configured to receive an end of a fluid line extending from the dialysis machine. The lid is configured to be coupled to the chamber to form a seal with the chamber. The inlet line has first end configured to be coupled to the chamber and a second end configured to be coupled to a fluid line of the dialysis machine. The outlet line has a first end configured to be coupled to the chamber and a second end configured to be coupled to a drain line of the dialysis machine. The valve is coupled to the outlet line and configured to control flow of fluid through the outlet line.

In a further aspect, a method includes emptying contents of a blood line set of a dialysis system into a chamber of a drain apparatus of the dialysis system, closing a lid of the drain apparatus to seal the chamber of the drain apparatus, flowing a disinfectant fluid through an inlet line of the drain apparatus from a dialysis machine of the dialysis system to the drain apparatus to at least partially fill the chamber of the drain apparatus with the disinfectant fluid, and flowing the disinfectant fluid through an outlet line of the drain apparatus from the drain apparatus to a drain line of the dialysis machine.

Implementations can include one or more of the following features.

In some implementations, the fluid line and the drain line are parts of a hydraulic circuit of the dialysis machine and the dialysis system further includes a dialyzer connected to the hydraulic circuit of the dialysis machine.

In certain implementations, the drain line is downstream of the dialyzer.

In some implementations, the fluid line is upstream of the dialyzer.

In certain implementations, the second end of the outlet line is configured to be coupled to the drain line at a location upstream of a post-dialyzer flow pump of the dialysis machine.

In some implementations, the second end of the outlet line is configured to be coupled to the drain line at a location of the dialysis machine downstream of a drain valve of the dialysis machine.

In certain implementations, the drain apparatus further includes a pump coupled to outlet line and configured to pump fluid from the chamber of the drain apparatus to the drain line of the dialysis machine.

In some implementations, the drain apparatus is configured to drain fluid contained in the chamber of the drain apparatus through the outlet line of the drain apparatus to the drain line of the dialysis machine by gravity when the valve of the drain apparatus is in an open position.

In certain implementations, the second end of the inlet line is configured to be coupled to a portion of the fluid line downstream of a fluid filter of the dialysis machine.

In some implementations, the drain apparatus includes a lid coupled to the chamber and configured to form a seal with the chamber.

In certain implementations, the lid includes a vent and a hydrophobic filter disposed within the vent.

In some implementations, the chamber includes an inner funnel coupled to and nested within an outer funnel.

In certain implementations, the inner funnel and outer funnel form an annular channel and the first end of the inlet line is fluidly connected to the annular channel.

In some implementations, the annular channel is formed between an outer surface of the inner funnel and an inner surface of the outer funnel.

In certain implementations, the drain apparatus further includes a pump coupled to the outlet line.

In some implementations, the drain apparatus further includes one or more mechanical attachment devices coupled to the chamber and configured to position the end of a patient line extending from the dialysis machine inside the chamber.

In certain implementations, the drain apparatus further includes a vent extending through the lid, and a hydrophobic membrane coupled to the vent.

In some implementations, the drain apparatus further includes a sensor configured to detect a fluid level in the chamber.

In certain implementations, the sensor includes a pressure sensor coupled to the outlet line.

In some implementations, the sensor includes an ultrasound sensor coupled to the chamber.

In certain implementations, sensor includes an ultrasonic sensor and an ultrasonic receiver coupled to the lid.

In some implementations, the sensor includes a light transmitter and a light receiver coupled to the lid.

In certain implementations, the sensor includes one or more electrodes coupled to the chamber.

In some implementations, the lid includes one or more vent holes.

In certain implementations, emptying contents of a blood line set of a dialysis system into a chamber of a drain apparatus of the dialysis system includes connecting a patient line of the blood line set to the drain apparatus of the dialysis machine following performance of dialysis on a patient, flowing a saline solution through the patient line of the blood line set into the drain apparatus to flush remaining fluid in the blood line set into the drain apparatus, and disconnecting the patient line of the blood line set from the drain apparatus.

In some implementations, the method further includes stopping flow of the disinfectant fluid upon receiving a signal from a sensor coupled to the drain apparatus indicating that the chamber of the drain apparatus is filled with disinfectant solution.

In certain implementations, the disinfectant fluid dwells in the chamber of the drain apparatus for a predetermined amount of time.

In some implementations, flowing the disinfectant fluid through the outlet line of the drain apparatus from the drain apparatus to the drain line of the dialysis machine includes opening a valve coupled to the outlet line of the drain apparatus.

In certain implementations, flowing the disinfectant fluid through the outlet line of the drain apparatus from the drain apparatus to the drain line of the dialysis machine includes pumping the disinfectant fluid in the chamber of the drain apparatus to the drain line using a pump coupled to the outlet line of the drain apparatus.

In some implementations, flowing the disinfectant fluid through the outlet line of the drain apparatus from the drain apparatus to the drain line of the dialysis machine includes using negative pressure generated by a flow pump of the dialysis machine to pump the disinfectant fluid in the chamber of the drain apparatus to the drain line.

In certain implementations, the disinfectant fluid includes a chemical disinfectant.

In some implementations, the disinfectant fluid is hot water.

In certain implementations, flowing the disinfectant fluid through the inlet line of the drain apparatus from the dialysis machine to the drain apparatus to at least partially fill the chamber of the drain apparatus includes flowing the disinfectant fluid into the chamber at a rate sufficient to maintain a predetermined level of fluid in the chamber for a predetermined amount of time.

Advantages of the systems, devices, and methods described herein include ease of use for the user. By providing a drain apparatus that is coupled to the drain line of the dialysis machine, emptying and disinfecting the drain apparatus following priming or flushing patient lines is simplified by reducing the need to drain and sterilize the drain apparatus separately from the dialysis machine. Another advantage is that by incorporating the disinfection of the drain apparatus used for priming and flushing patient lines with disinfection of the dialysis machine, the overall time required to disinfect the drain apparatus and the dialysis machine is reduced. Another advantage is a reduced risk of spills and biohazards. For example, since the drain apparatus can be disinfected and drained while remaining connected to the dialysis machine, the need to transport the drain apparatus for disinfection, and thus risk spilling the contents of drain apparatus (e.g., patient line fluids), is greatly reduced.

Other aspects, features, and advantages will be apparent from the description and drawings, and from the claims.

DETAILED DESCRIPTION

Figure 1:
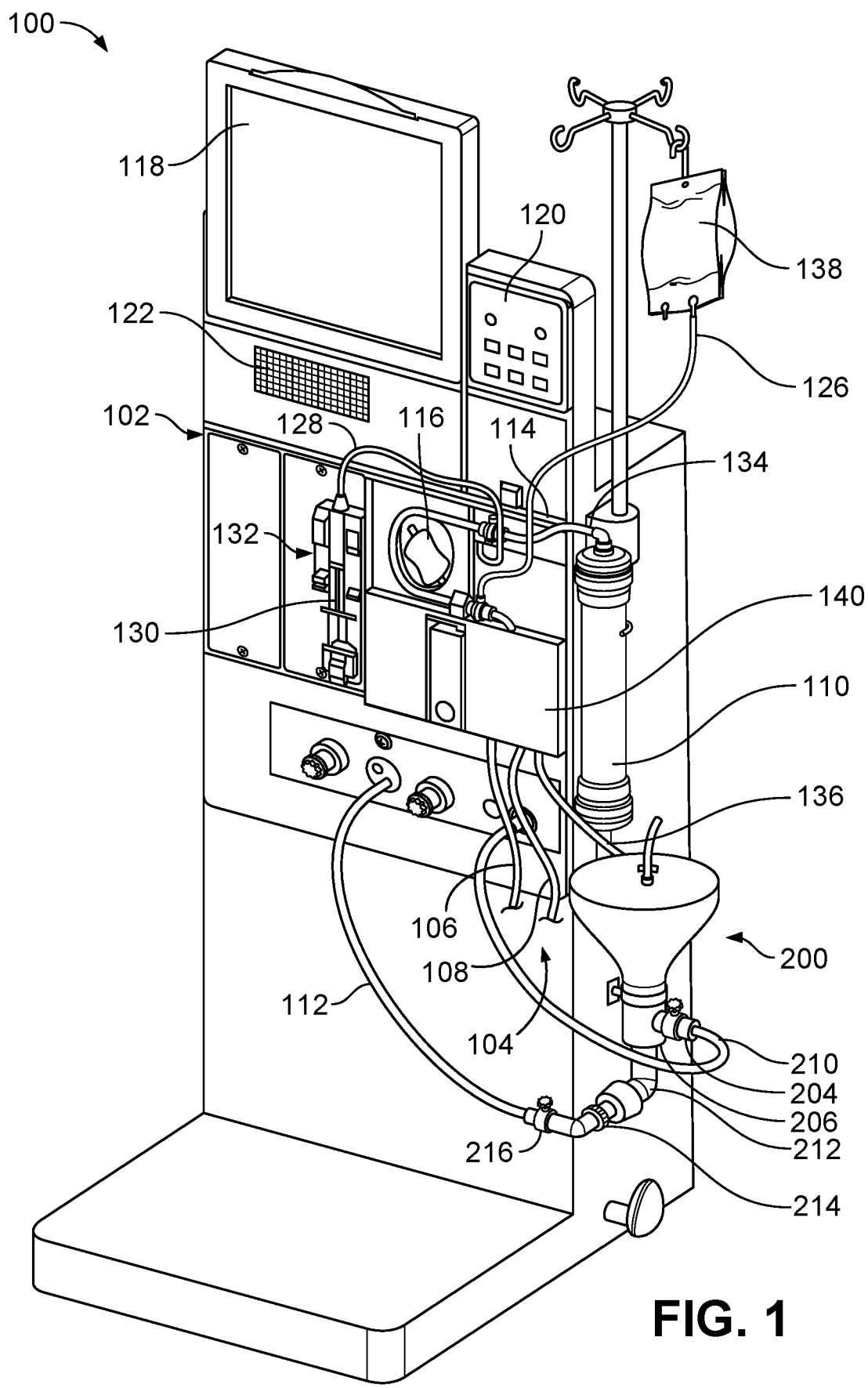
FIG. 1 is a perspective view of a hemodialysis system that includes a drain apparatus coupled to a dialysis machine.

Referring to FIG. 1, a hemodialysis system 100 includes a hemodialysis machine 102 to which a disposable blood component set 104 that forms a blood circuit is connected. During hemodialysis, arterial and venous patient lines 106, 108 of the blood component set 104 are connected to a patient and blood is circulated through various blood lines and components, including a dialyzer 110, of the blood component set 104. At the same time, dialysate is circulated through a dialysate circuit (shown in FIG. 5) formed by the dialyzer 110 and various other dialysate components and fluid lines connected to the hemodialysis machine 102. Many of these dialysate components and fluid lines are located inside the housing of the hemodialysis machine 102, and are thus not visible in FIG. 1. The dialysate passes through the dialyzer 110 along with the blood. The blood and dialysate passing through the dialyzer 110 are separated from one another by a semi-permeable structure (e.g., a semi-permeable membrane and/or semi-permeable microtubes) of the dialyzer 110. As a result of this arrangement, toxins are removed from the patient's blood and collected in the dialysate. The filtered blood exiting the dialyzer 110 is returned to the patient. The dialysate that exits the dialyzer 110 includes toxins removed from the blood and is commonly referred to as "spent dialysate." The spent dialysate is routed from the dialyzer 110 to a drain via a drain line 112.

Still referring to FIG. 1, the dialysate circuit of the hemodialysis machine 102 is formed by multiple dialysate components and fluid lines positioned inside the housing of the hemodialysis machine 102 as well as the dialyzer 110, a dialyzer inlet line 134, and a dialyzer outlet line 136 that are positioned outside of the housing of the hemodialysis machine 102. The dialyzer inlet line 134 includes a connector adapted to connect to one end region of the dialyzer 110, and the dialyzer outlet line 136 includes a connector adapted to connect to another end region of the dialyzer 110.

Still referring to FIG. 1, the hemodialysis machine 102 includes a touch screen 118 and a control panel 120. The touch screen 118 and the control panel 120 allow the operator to input various different treatment parameters to the hemodialysis machine 102 and to otherwise control the hemodialysis machine 102. In addition, the touch screen 118 serves as a display to convey information to the operator of the hemodialysis system 100. A speaker 122 is positioned below the touch screen 118 and functions to provide audio signals to the operator of the system 100. Thus, the hemodialysis machine 102 is capable of providing both visual alerts via the touch screen 118 and audio alerts via the speaker 122 to the operator of the system 100 during use.

The blood component set 104 of the hemodialysis system is secured to a module 114 attached to the front of the hemodialysis machine 102. The module 114 includes a blood pump 116 capable of driving blood through the blood circuit. The module 114 also includes various other instruments capable of monitoring the blood flowing through the blood circuit. The module 114 includes a door 140 that when closed, as shown in FIG. 1, cooperates with the front face of the module 114 to form a compartment sized and shaped to receive the blood component set 104. In the closed position, the door 140 presses certain blood components of the blood component set 104 against corresponding instruments exposed on the front face of the module 114. This arrangement facilitates control of the flow of blood through the blood circuit and monitoring of the blood flowing through the blood circuit.

As depicted in FIG. 1, the hemodialysis system 100 also includes a drain apparatus 200 coupled to the hemodialysis machine 102. The drain apparatus 200 includes a lid 202, an inlet port 204, an outlet port 206, an inlet line 210, an outlet line 212, a drain apparatus pump 214, and an outlet valve 216.

In some implementations, the lid 202 is coupled to the body of the drain apparatus 200 with a hinge. During use, the lid 202 of the drain apparatus 200 may be opened and the venous patient line 108 of the blood component set 104 may be placed within a chamber of the drain apparatus 200 to expel fluid from the venous patient line 108 into the chamber of the drain apparatus 200.

The components of the hemodialysis machine 102 and the drain apparatus 200 can be disinfected between treatments. For example, a disinfectant fluid can be provided to and circulated through the hydraulic circuit of the hemodialysis machine 102 and the drain apparatus 200 between treatments in order to disinfect the hemodialysis machine 102 and drain apparatus 200. As described in further detail herein, the drain apparatus 200, when not in use, can be disinfected by closing the lid 202 and flowing disinfection fluid through the chamber of the drain apparatus 200.

Figure 2:
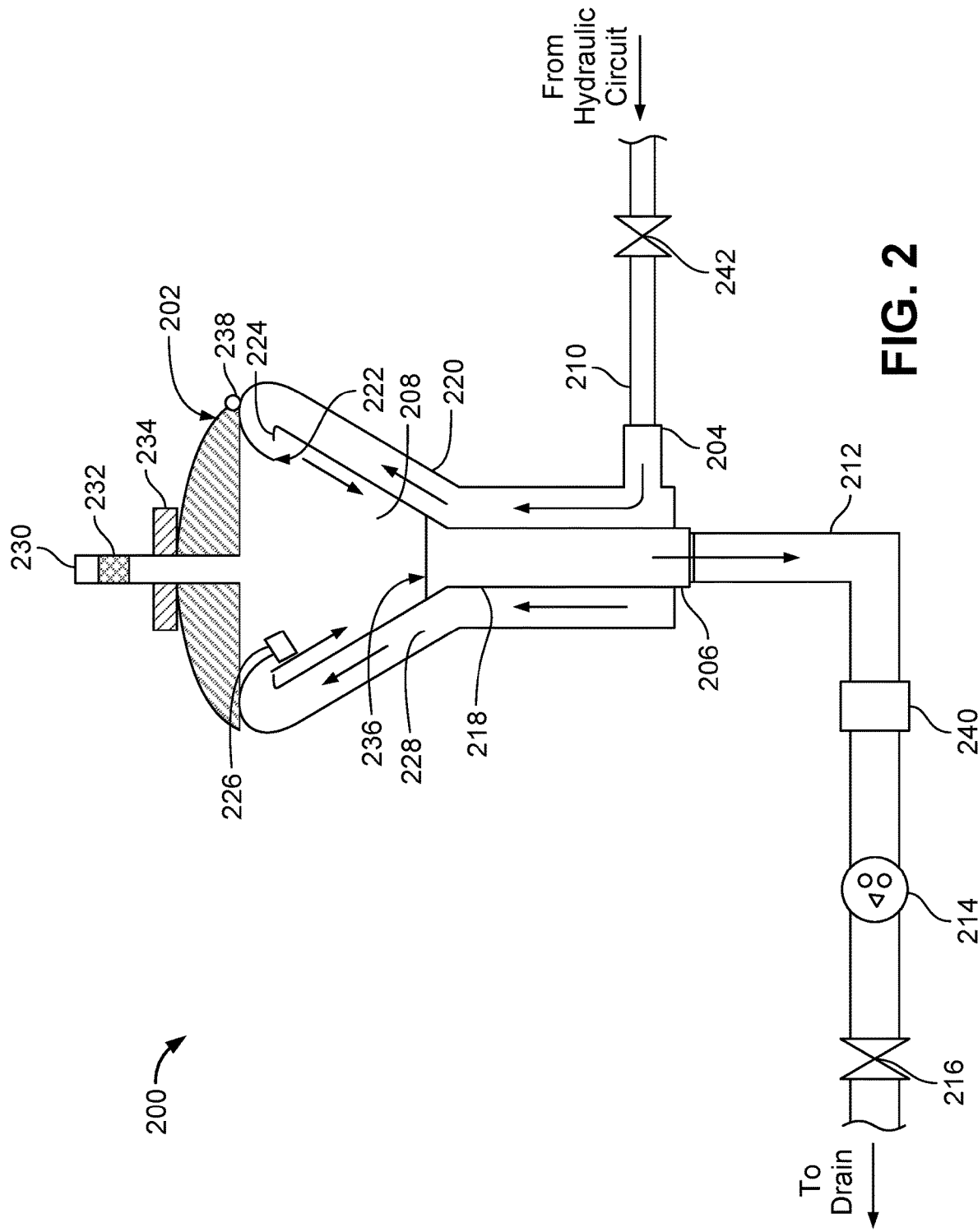
FIG. 2 is a cross-sectional view of the drain apparatus of FIG. 1.

FIG. 2 depicts a cross section view of the drain apparatus 200 with the lid 202 closed. As depicted in FIG. 2, the drain apparatus includes an inner funnel 218 and an outer funnel 220. The inner funnel 218 forms a chamber 208 within the drain apparatus 200 configured to receive and collect liquid. The outer funnel 220 includes an upper lip 222 that encompasses an annular surface 224 of the inner funnel 218. The inner funnel 218 of the drain apparatus 200 is nested within and connected to an outer funnel 220 of the drain apparatus 200. As shown in FIG. 2, the inner funnel 218 is connected to the outer funnel 220 proximate the outlet port 206 of the drain apparatus 200. The inner funnel 218 can be connected to the outer funnel 220 by any suitable techniques, such as welding, injection molding, etc.

The nested arrangement of the inner funnel 218 and the outer funnel 220 creates an annular channel 228 between the inner funnel 218 and the outer funnel 220 that surrounds the inner funnel 218. Fluid received through the inlet port 204 from the inlet line 210 can travel through the annular channel 228 between the inner funnel 218 and the outer funnel 220, over the annular surface 224 of the inner funnel 218, and into the chamber 208 of the drain apparatus. Arranging the inner funnel 218 and outer funnel 220 to create a 360 degree annular channel 228 enables fluid to be fairly evenly distributed to the entire surface of the chamber 208 of the drain apparatus 200. In some examples, the inner funnel 218 and outer funnel 220 are arranged to form an annular channel 228 with a width of about 0.125 inches to about 0.25 inches.

The inner funnel 218 and the outer funnel 220 of the drain apparatus 200 can be formed of any of various different medical grade materials. Examples of such materials include PVC, polyethylene, polypropylene, silicone, polyurethane, high density polyethylene, nylon, ABS, acrylic, isoplast, polyisoprene, polycarbonate, stainless steel, glass, titanium, carbon fiber, and porcelain.

As shown in FIG. 2, a clip 226 is attached to the upper lip 222 of the outer funnel 220. The clip 226 is configured to receive the venous patient line 108 of the hemodialysis system 100 and to position a patient end of venous patient line 108 within the chamber 208 of the drain apparatus. As described in the further detail herein, the chamber 208 is configured to collect fluids contained within the blood lines and provide the collected fluids to a drain via the outlet line 212 of the drain apparatus 200.

Still referring to FIG. 2, the drain apparatus 200 also includes a screen 236 located within and coupled to the inner funnel 218 of the drain apparatus 200. The screen 236 is configured to prevent particulates above a defined size from entering, and potentially obstructing, the outlet line 212. For example, the screen 236 includes a plurality of openings sized to allow fluid to flow through the screen 236 while preventing particulates above a defined size from entering the outlet line 212. In some examples, the screen 236 includes openings with a diameter of about 0.10 inches to about 0.15 inches (e.g., 0.125 inch diameter). The screen 236 is positioned in a location within the chamber 208 that prevents blood lines positioned within the chamber 208 using the clip 226 from contacting the screen 236. In some implementations, the screen 236 is removable and can be removed from the drain apparatus 200 for cleaning. The screen 236 can be formed of any of various different medical grade materials. Examples of such materials include PVC, polyethylene, polypropylene, silicone, polyurethane, high density polyethylene, nylon, ABS, acrylic, isoplast, polyisoprene, polycarbonate, stainless steel, titanium, and carbon fiber.

As shown in FIG. 2, the lid 202 of the drain apparatus 200 includes a vent 230 with a hydrophobic filter 232. The vent 230 extends through the lid 202 to outside the drain apparatus 200. A coupler 234 is coupled to the vent 230 to create a fluid seal between the vent 230 and the lid 202. The hydrophobic filter 232 is arranged within the vent 230. As described in further detail herein, as the chamber 208 of the drain apparatus 200 is filled with fluid, air contained within the chamber 208 is displaced by the fluid and exits out the vent 230, allowing for complete filling of the chamber 208. Further, the hydrophobic filter 232 prevents liquids provided to the chamber 208 from exiting through the vent 230. The hydrophobic filter 232 may be made of a hydrophobic material, such as polytetrafluoroethylene (PTFE) (e.g., expanded polytetrafluoroethylene (ePTFE)), a blend of polyethylene and carboxymethylcellulose, etc. In certain implementations, the hydrophobic filter 232 is a fibrous carrier with a matted and woven layer on top of which ePTFE or other micro-porous material is applied. The vent 230 can includes a plurality of pores, each pore having a diameter of about 15 μm to about 45 μm (e.g., 30 μm). In some examples, a material of the vent 230 expands in response to contacting fluid, which closes the plurality of pores in the vent 230 and prevents fluid from passing through the vent 230.

Still referring to FIG. 2, the inlet port 204 of the drain apparatus 200 is coupled to the inlet line 210. In some implementations, the inlet line 210 is coupled to the inlet port 204 using a coupler. The inlet line 210 can be coupled to the inlet port 204 using a metal band or plastic band that restricts the tubing of the inlet line 210 around a barb of the inlet port 204. A first end of the inlet line 210 is coupled to the inlet port 204 and a second end of the inlet line 210 is coupled to a fluid line of the hemodialysis machine 102.

In the implementation shown in FIG. 2, a drain apparatus inlet valve 242 is fluidly connected to the inlet line and is configured to control the flow of fluids into the chamber 208 via the inlet line 210. The drain apparatus inlet valve 242 can be communicatively coupled to the hemodialysis machine 102 and can be opened and closed in response to signals received from the hemodialysis machine 102. An example of a suitable valve is a solenoid valve.

The outlet port 206 of the drain apparatus 200 is coupled to the outlet line 212. In some implementations, the outlet line 212 is coupled to the outlet port 206 using a coupler. The outlet line 212 can be coupled to the outlet port 206 using a metal band or plastic band that restricts the tubing of the outlet line 212 around a barb of the outlet port 206. As described in further detail herein, a first end of the outlet line 212 is coupled to the outlet port 206 and a second end of the outlet line 212 is coupled to a drain line 112 of the hemodialysis machine 102.

The drain apparatus outlet valve 216 is fluidly connected to the outlet line 212 of the drain apparatus 200 and is configured to control the flow of fluid from the outlet line 212 to the drain line 112. In some implementations, the drain apparatus outlet valve 216 is communicatively coupled to the hemodialysis machine 102 and can be opened and closed in response to signals received from the hemodialysis machine 102. An example of a suitable valve is a solenoid valve.

As shown in FIG. 2, the drain pump 214 is fluidly coupled to the outlet line 212 of the drain apparatus 200. The drain pump 214 is configured to pump fluid from the chamber 208 of the drain apparatus 200 through the outlet line 212 to the drain line 112 of the hemodialysis machine 102. Any of various suitable pumps can be used, such as a peristaltic pump, a piston pump, an impeller pump, a magnetically driven gear pump, etc.

The inlet line 210 and the outlet line 212 of the drain apparatus 200 can be formed of any of various different medical grade materials. Examples of such materials include PVC, polyethylene, polypropylene, silicone, polyurethane, high density polyethylene, nylon, ABS, acrylic, isoplast, polyisoprene, and polycarbonate.

Still referring to FIG. 2, a pressure sensor 240 is coupled to the outlet line 212 of the drain apparatus 200 proximate the outlet port 204. The pressure sensor 240 is configured to measure the fluid pressure in the chamber 208 of the drain apparatus 200. For example, the pressure inside the chamber 208 can be measured by the pressure sensor 240 while the chamber 208 is being filled with disinfectant fluid in order to determine when the chamber 208 is filled with disinfectant fluid based on the pressure in the chamber 208. In some implementations, the pressure sensor 240 is an inline pressure transducer. Other types of pressure sensors that can be used include other types of pressure transducers, such as an M3200 pressure transducer.

Figure 3:
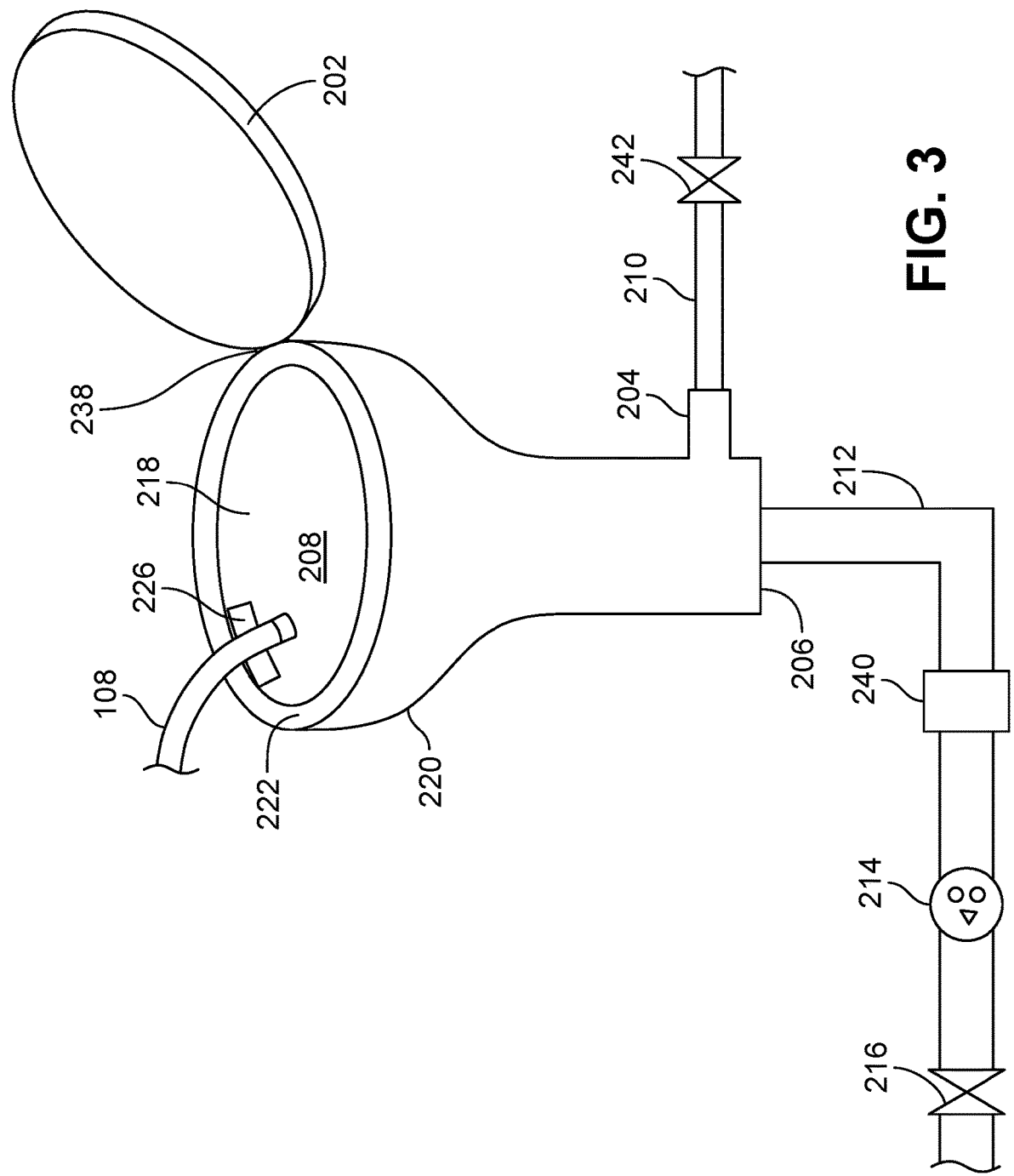
FIG. 3 is a perspective view of the drain apparatus of FIG. 1 in an open position with a patient line of a hemodialysis system coupled to the drain apparatus.
Figure 4:
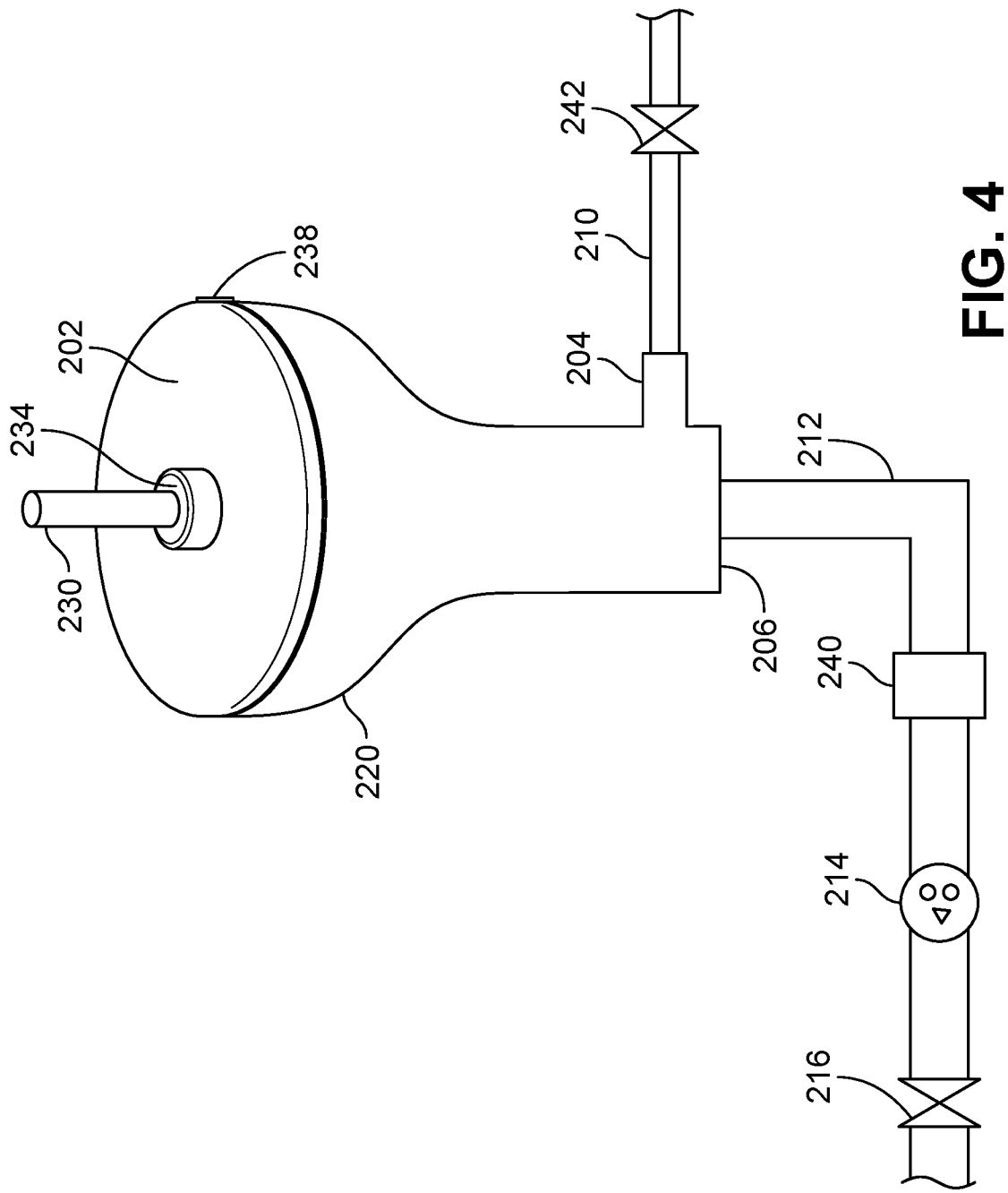
FIG. 4 is a perspective view of the drain apparatus of FIG. 1 in a closed position FIG. 5 a schematic of a dialysate circuit of the hemodialysis system of FIG. 1 with the drain apparatus of coupled to the dialysate circuit.

FIG. 3 depicts a perspective view of the drain apparatus 200 of FIG. 1 with the lid 202 of the drain apparatus 200 in an open position and the venous patient line 108 attached to the drain apparatus 200 via the clip 226. FIG. 4 depicts a perspective view of the drain apparatus 200 with the lid 202 in the closed position. As depicted in FIGS. 3 and 4, the lid 202 is attached to the outer funnel 220 by a hinge 238 such that the lid 202 can be moved between the open position depicted in FIG. 3 and the closed position depicted in FIG. 4. The lid 202 forms a seal with the outer funnel 220 to seal the chamber 208 when in the closed position to prevent fluids from escaping the top of the chamber 208. The lid 202 can be opened or closed based on the process being performed by the hemodialysis machine or the stage of hemodialysis treatment. For example, the lid 202 can be opened to receive the venous patient line 108 for draining contents of the line 108 into the drain apparatus. The lid 202 can be closed during disinfection of the drain apparatus 200, as described in further detail herein.

As previously discussed, the dialysate circuit of the hemodialysis machine 102 of FIG. 1 is formed by multiple dialysate components and fluid lines positioned inside the housing of the hemodialysis machine 102 as well as the dialyzer 110, the dialyzer inlet line 134, and the dialyzer outlet line 136 that are positioned outside of the housing of the hemodialysis machine 102.

Figure 5:
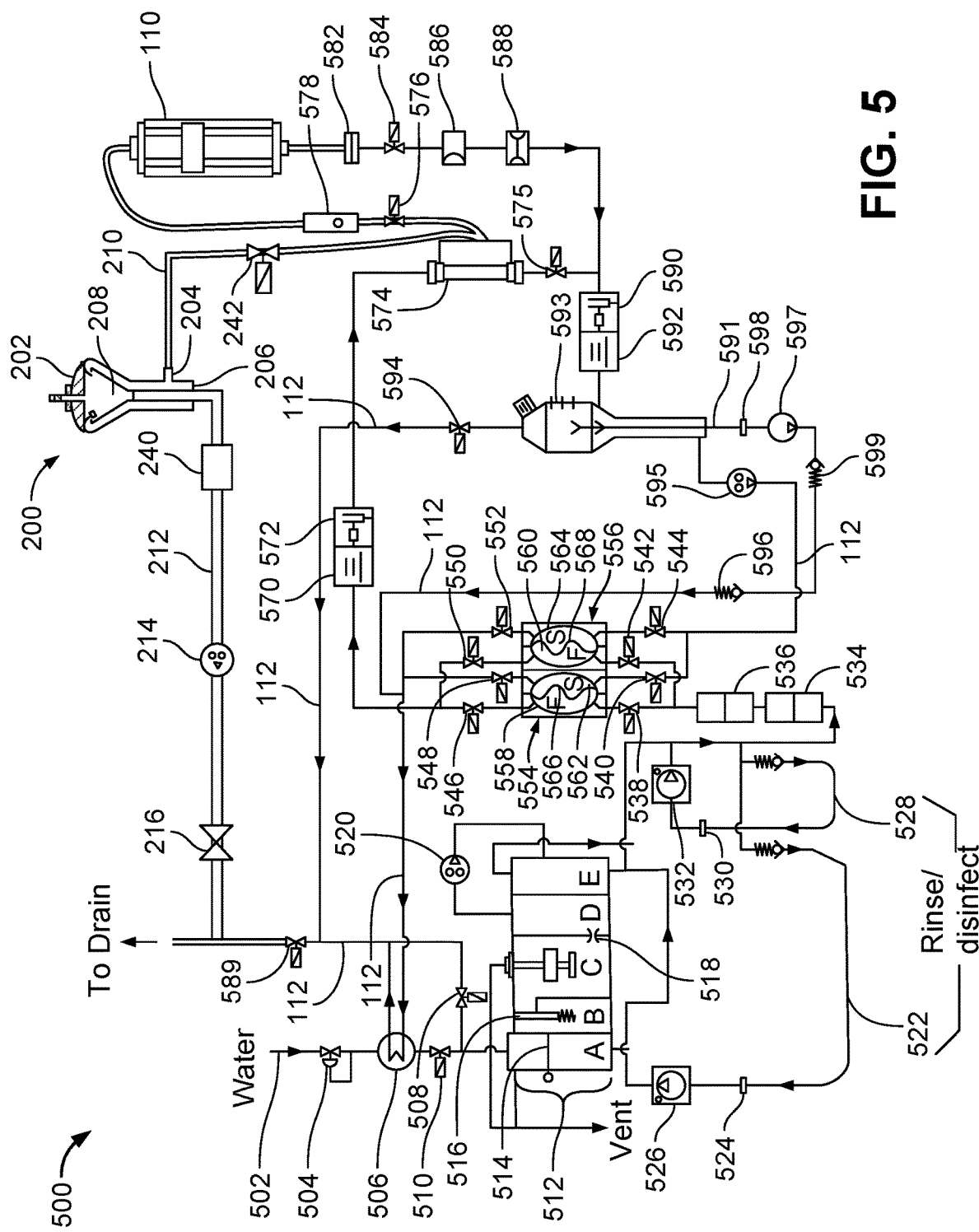

FIG. 5 is a schematic showing the flow paths of fluids into, through, and out of the dialysate circuit 500. The dialysate circuit 500 includes a number of dialysate components that are fluidly connected to one another via a series of fluid lines and the drain line 112.

Still referring to FIG. 5, a water inlet port 502 is configured to receive water from an external source and provide the water to a heat exchanger 506 via the fluid line. Heat exchanger 506 is configured to warm the water received by the dialysate circuit 500 through the water inlet port 502 using the heat of spent dialysate (or other fluid) flowing on an opposite side of the heat exchanger 506.

After exiting the heat exchanger 506, the warmed water flows to the deaeration and heating chamber 512. The deaeration and heating chamber 512 is configured to heat and deaerate water received by the dialysate circuit 500 through the water port 502. The heating and deaeration chamber 512 includes a temperature control thermistor 514 for monitoring the temperature of the heated water and a heater 516 to increase the temperature of the water received by the chamber 512. For example, if the temperature of the water received by the deaeration and heating chamber 512 is below a threshold temperature, as detected by temperature control thermistor 514, the heater 516 can be used to heat the water above the threshold temperature. An aeration orifice 518 is positioned between two of the sub-chambers 512C, 512D and is configured deaerate the flow of water as the deaeration pump 520 pumps the water from sub-chamber 512A to sub-chamber 512E.

The warmed and deaerated water flows from sub-chamber 512E to mixing chambers 534, 536 where the water, acid concentrate, and bicarbonate concentrate are mixed. The dialysate circuit 500 includes an acid concentrate pump 526 coupled to a source of acid concentrate. The acid concentrate pump 526 is configured to pump acid concentrate into the flow of water travelling from the deaeration and heating chamber 512 to the mixing chambers 534, 536.

The dialysate circuit 500 also includes a bicarbonate pump 532 that is coupled to a source of bicarbonate. The bicarbonate pump 532 is configured to pump bicarbonate into the flow of water and acid concentrate between the deaeration and heating chamber 512 and the mixing chamber 534, 536.

The mixing chambers 534, 536 are fluidly connected to a fluid line downstream of the acid concentrate pump 526 and bicarbonate pump 532, and are configured to receive the combined flow of heated water, acid concentrate, and bicarbonate and mix the fluids to generate a uniform dialysate fluid. As shown in FIG. 5, the mixing chambers 534, 536 are arranged serially to ensure thorough mixing of the dialysate solution.

Balancing devices 554, 556 are fluidly connected to a fluid line downstream of the mixing chambers 534, 536. The balancing devices 554, 556 each include a spherical chamber that is divided into a first chamber half 558, 560 and a second chamber half 562, 564 by a flexible membrane 566, 568. As fluid flows into the first chamber halves 558, 560, fluid is forced out of the second chamber halves 562, 564, and vice versa. Valves 538 through 552 are used to control the flow of dialysate into and out of the balancing devices 554, 556 such that as fresh dialysate is flowing into one balancing device 554, spent dialysate is flowing into the other balancing device 556, and vice versa. For example, as spent dialysate flows into the second chamber half 562 of balancing device 554 and forces fresh dialysate to flow out of first chamber half 558 of balancing device 554 towards the dialyzer 110, fresh dialysate flows into first chamber half 560 of balancing device 556 and forces spent dialysate to flow out of the second chamber half 564 of balancing device 556 towards the drain, and vice versa. This alternation of fresh and spent dialysate flowing into the balancing chambers 554, 556 is controlled by valves 538 through 552. This balancing device construction and alternating flow of fresh and spent dialysate helps to ensure that the volume of fluid entering the balancing devices 554, 556 is equal to the volume of fluid exiting the balancing devices 554, 556. This helps to ensure that the volume of fresh dialysate entering the dialysate circuit is equal to the volume of spent dialysate exiting the dialysate circuit when desired during treatment, as described in greater detail below.

During hemodialysis, fresh dialysate passing through the first chamber halves 558, 560 of the balancing devices 554, 556 is directed to the dialyzer 110 through a dialysate filter 574. Prior to filtration by dialysate filter 574, the fresh dialysate flows through a conductivity cell 570 and a temperature monitor thermistor 572 downstream of the of the balancing devices 554, 556. The conductivity cell 570 and temperature monitor thermistor 572 regulate the temperature of the fresh dialysate entering the filter 574 and dialyzer 110. The fresh dialysate flowing out of balancing devices 554, 556 flows along a fluid line through the dialysate filter 574, which is configured to filter the fresh dialysate received from the balancing devices 554, 556 prior to providing the dialysate to the dialyzer 110. One example of such a dialysate filter 574 is the DIASAFE®plus dialysis fluid filter available from Fresenius Medical Care filter. During hemodialysis, a bypass valve 575 is closed and a dialyzer inlet valve 576 is open in order to direct the flow of dialysate from the dialysis filter 574 to the dialyzer 110.

During hemodialysis, the fresh dialysate flowing out of the first chamber halves 558, 560 of the balancing devices 554, 556 is directed through the dialyzer 110 toward the air separation chamber 593. Spent dialysate exits the dialyzer 110 along a drain line 112 of the dialysate circuit 500. A pressure sensor 586 located along the drain line 112 connecting the dialyzer 110 to the air separation chamber 593 is adapted to measure the pressure of the spent dialysate exiting the dialyzer 110. Any of various different types of pressure sensors capable of measuring the pressure of the spent dialysate passing from the dialyzer 110 to the air separation chamber 593 can be used.

The spent dialysate exiting the dialyzer 110 collects in the air separation chamber 593. The air separation chamber 593 uses an air sensor coupled to the air separation chamber 593 to detect air contained within the spent dialysate, and the air separation chamber 593 vents off any air contained with the spent dialysate. Air detected in the spent dialysate by the equalizing chamber travels through the vent valve 594 to the drain.

A dialysate flow pump 595 is configured to pump the spent dialysate from the air separation chamber 593 through a fluid line to the second chamber halves 562, 564 of the balancing devices 554, 556. As previously discussed, the flow of spent dialysate into the balancing devices 554, 556 is controlled by valves 540 and 544 to alternate the flow of spent dialysate between each of the second chamber halves 562, 564 of the balancing devices 554, 556.

As one of the second chamber halves 562, 564 of one of the balancing devices 554, 556 fills with the spent dialysate, fresh dialysate within the first chamber half 558, 560 of the respective balancing device 554, 556 is expelled towards the dialyzer 110. Subsequently, as the first chamber half 558, 560 of the respective balancing device 554, 556 is refilled with fresh dialysate, the spent dialysate is forced out the second chamber half 562, 564 of the respective balancing device 554, 556 is through one of valves 548, 552, respectively, via drain line 112 to the drain. As previously discussed, as fresh dialysate is flowing into one balancing device 554, spent dialysate is flowing into the other balancing device 556, and vice versa.

As shown in FIG. 5, an ultrafiltration line 591 is connected to an outlet of the air separation chamber 593. An ultrafiltration pump 597 is operatively connected to the ultrafiltration line 591 such that when the ultrafiltration pump 597 is operated, spent dialysate can be pulled from the air separation chamber 593 and directed to the drain via the ultrafiltration line 591. Operation of the ultrafiltration pump 597 while simultaneously operating the dialysate flow pump 595 causes increased vacuum pressure within the line connecting the air separation chamber 593 to the dialyzer 110, and thus creates increased vacuum pressure within the dialyzer 110. As a result of this increased vacuum pressure, additional fluid is pulled from the blood circuit into the dialysate circuit across the semi-permeable structure (e.g., semi-permeable membrane or semi-permeable microtubes) of the dialyzer 110. Thus, the ultrafiltration pump 597 can be operated to remove excess fluid from the patient.

As shown in FIG. 5, the inlet line 210 of the drain apparatus is connected to a fluid line of the dialysate circuit downstream of the dialysate filter 574 and upstream of the dialyzer 110. The dialyzer inlet valve 576 along a fluid line downstream of the dialysate filter 574 can be closed in order to direct flow of fluid exiting the dialysate filter 574 to the inlet line 210 and chamber 208 of the drain apparatus 200.

Still referring to FIG. 5, the outlet line 212 of the drain apparatus 200 is coupled to drain line 112 downstream of the drain valve 589 of the drain line 112. As previously discussed, a drain apparatus outlet valve 216 is positioned along the outlet line 212. When the valve 216 is closed, fluid provided to the chamber 208 through the inlet line 210 collects in the chamber 208 of the drain apparatus 200. In some examples, fluid is continuously provided from a fluid line of the dialysate circuit 500 to the drain apparatus 200 via the inlet line 210 until the pressure sensor 240 positioned along the outlet line 212 detects a pressure in the chamber 208 of the drain apparatus 200 indicating that the chamber 208 is full of fluid. Opening the valve 216 allows fluid collected in the chamber 208 of the drain apparatus 200 to flow through the outlet line 212 to the drain line 112. For example, after a heated disinfectant fluid provided to the chamber 208 via the inlet line 210 has been allowed to dwell in the chamber 208 for a predetermined amount of time, the valve 216 can be opened to drain the disinfectant fluid from the chamber 208 to the drain line 112. The drain apparatus pump 214 positioned along the outlet line 212 can also be used to pump fluid from the chamber 208 of the drain apparatus 200 to the drain line 112 via the outlet line 212.

The various fluid lines and drain line 112 of the dialysate circuit 500, as well as the lines 210 and 212, can be formed of any of various different medical grade materials. Examples of such materials include PVC, polyethylene, polypropylene, silicone, polyurethane, high density polyethylene, nylon, ABS, acrylic, isoplast, polyisoprene, and polycarbonate.

Figure 6:
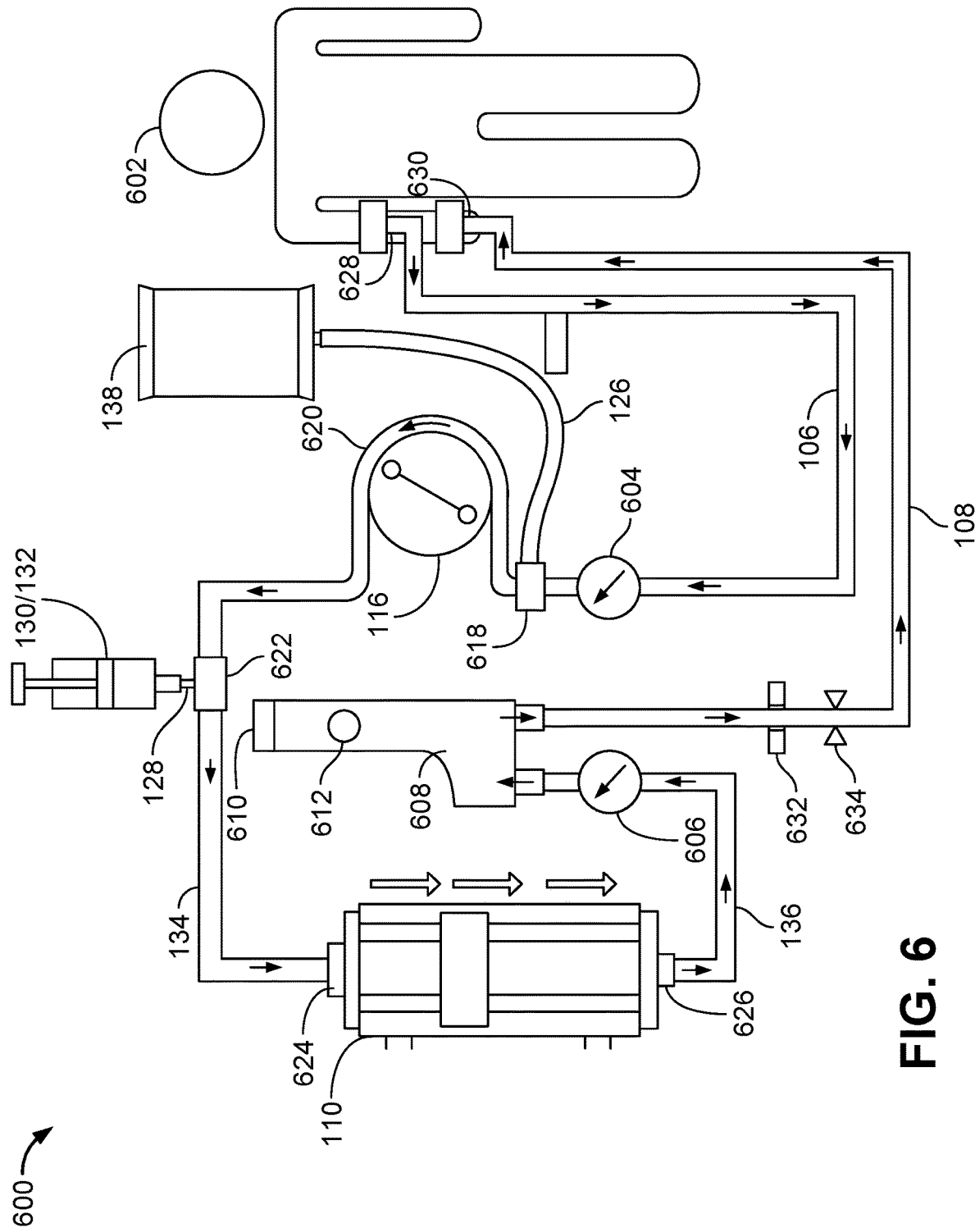
FIG. 6 is a schematic of a blood circuit of the hemodialysis system of FIG. 1.

FIG. 6 is a schematic showing the flow paths of fluids into, through, and out of the blood circuit 600 of the hemodialysis system 100. During hemodialysis treatment, one end 628 of the arterial patient line 106 is fluidly connected to an artery of a patient 602. The arterial patient line 106 is also fluidly connected to an arterial pressure sensor 604. Arterial pressure sensor 604 is fluidly connected to the arterial patient line 106 and is configured to measure the pressure of the blood flowing the arterial patient line 106. As shown in FIG. 6, the arterial pressure sensor 604 is positioned upstream of the blood pump 116 to measure a pre-pump arterial pressure. Upon detecting that the pressure within the blood circuit 600 has dropped below a certain level, the arterial pressure sensor 604 can transmit a signal to that effect to the hemodialysis machine 102, which can activate an audio and/or visual alarm to alert the operator of the system of a drop in blood pressure of the patient 602. In some implementations, the arterial pressure sensor 604 is provided as combination of a pressure transducer aligned with a pressure sensor capsule. For example, a pressure transducer may be positioned on a door 140 of the module 114 such that when the door 140 is closed, the pressure transducer presses against the pressure capsule and can measure the pressure of blood flowing through the capsule. For example, as the fluid pressure changes within the pressure sensor capsule, the amount of pressure applied to the pressure transducer by the pressure sensor capsule also changes.

The arterial patient line 106 extends from the patient 602 to a first pump line adaptor 618, which connects the arterial patient line 106 to one end of a U-shaped pump line 620. The other end of the pump line 620 is connected to a second pump line adaptor 622, which is fluidly connected to a dialyzer inlet line 134. The dialyzer inlet line 134 is connected via a tube adaptor to a blood entry port 624 of the dialyzer 110. A blood exit port 626 of the dialyzer 110 is connected to another tube adaptor, which connects the dialyzer 110 to a dialyzer outlet line 136. The blood pump 116 pumps blood from the artery of the patient 602 through the arterial patient line 106 to the dialyzer 110.

A venous pressure sensor 606 is positioned along a dialyzer outlet line 136, upstream of an air release device 608 and is configured to monitor blood pressure on the venous side of the dialyzer 110. In some implementations, the venous pressure sensor 606 is provided as combination of a pressure transducer aligned with a pressure sensor capsule. For example, a pressure transducer may be positioned on a door 140 of the module 114 such that when the door 140 is closed, the pressure transducer presses against the pressure capsule and can measures the pressure of blood flowing through the capsule. For example, as the fluid pressure changes within the pressure sensor capsule, the amount of pressure applied to the pressure transducer by the pressure sensor capsule also changes.

As shown in FIG. 6, the dialyzer outlet line 136 is coupled to an air release device 608. The air release device 608 includes a vent assembly 610 located at the top of the air release device 608. The vent assembly 610 allows air to pass therethrough while inhibiting (e.g., preventing) liquid from passing therethrough. If blood passing through the blood circuit 600 during treatment contains air, the air will be vented to the atmosphere as the blood passes through the air release device 608.

In some implementations, the module 114 of the hemodialysis machine 102 includes a level detector 612 that aligns with the air release device 608 when the blood component set 104 is secured to the front face of the module 114. The level detector 612 is adapted to detect the level of liquid (e.g., blood and/or saline) within the air release device 608.

Still referring to FIG. 6, a venous patient line 108 is connected to an exit port of the air release device 608 at a first end and is fluidly connected to a vein of a patient 602 during treatment at a second end 630.

An air bubble detector 632 is positioned along the venous patient line 108 downstream of the air release device 608. The air bubble detector 632 is capable of detecting air bubbles within the venous patient line 108. The air bubble detector 632 includes a housing that forms a channel in which the venous patient line 108 is received. In some implementations, the door 140 of the module 114 of the hemodialysis machine 102 includes a fin that presses the venous patient line 108 into the channel of the housing and against a sensor of the air bubble detector 632 when the door 140 is closed.

An occluder 634 is positioned along the venous patient line 108 downstream of the air bubble detector 632. The occluder 634 is configured to crimp the portion of the venous patient line 108 disposed therein to prevent blood from passing through the venous patient line 108 when activated. The occluder 634 can, for example, be connected to the air bubble detector 632 so that the occluder 634 can be activated when the air bubble detector 632 detects an air bubble within the venous patient line 108. Such an arrangement helps to ensure that no air bubbles reach the patient in the event that the air release device 608 fails to remove one or more air bubbles from the blood. Similar to the air bubble detector 632, the occluder 634 includes a housing that forms a channel in which the venous patient line 108 is received. In some implementations, the door 140 of the module 114 includes a fin that presses the venous patient line 108 into the channel of the housing of the occluder 634 when the door 140 is closed.

In addition to the blood lines forming the main blood circuit 600, a saline delivery line 126 and a drug delivery line 128 can be connected to the blood circuit 600 for the introduction of saline and drugs (e.g., heparin), respectively, into the blood circuit 600. As depicted in FIG. 6, the saline delivery line 126 is connected at a first end to a saline bag 138 and at a second end to the first pump line adaptor 618.

The drug delivery line 128 is connected at a first end to a syringe 130, which can contain a drug to be provided to the patient 602, and at a second end to the second pump line adaptor 622. The syringe 130 may be coupled to a drug pump 132. The drug pump 132 is a syringe pump that includes a clamping mechanism configured to retain the syringe 130 of the blood component set 104. The drug pump 132 also includes a stepper motor configured to move the plunger of the syringe 130 along the axis of the syringe 130. A shaft of the stepper motor is secured to the plunger in a manner such that when the stepper motor is operated in a first direction, the shaft forces the plunger into the syringe 130, and when operated in a second direction, the shaft pulls the plunger out of the syringe 130. The drug pump 132 can thus be used to inject a liquid drug (e.g., heparin) from the syringe 130 into the blood circuit 600 via the drug delivery line 128 during use, or to draw liquid from the blood circuit 600 into the syringe 130 via the drug delivery line 128 during use.

The various blood lines, the saline delivery line 126, and the drug delivery line 128 can be formed of any of various different medical grade materials. Examples of such materials include PVC, polyethylene, polypropylene, silicone, polyurethane, high density polyethylene, nylon, ABS, acrylic, isoplast, polyisoprene, and polycarbonate.

The various blood lines, the saline delivery line 126, and the drug delivery line 128 are typically retained within the module 114. Various techniques can be used to secure the lines to the module 114. For example, a carrier body with a series of apertures and recesses for capturing and retaining the various blood lines and components can be secured to the module 114 of the hemodialysis machine 102. In some examples, mechanical attachment devices (e.g., clips or clamps) can be attached to a carrier body and used to retain the lines, and the carrier body can be attached to the module 114 of the hemodialysis machine 102. As another example, the lines can be adhered to or thermally bonded to a carrier body, and the carrier body can be attached to the module 114 of the hemodialysis machine.

Figure 16:
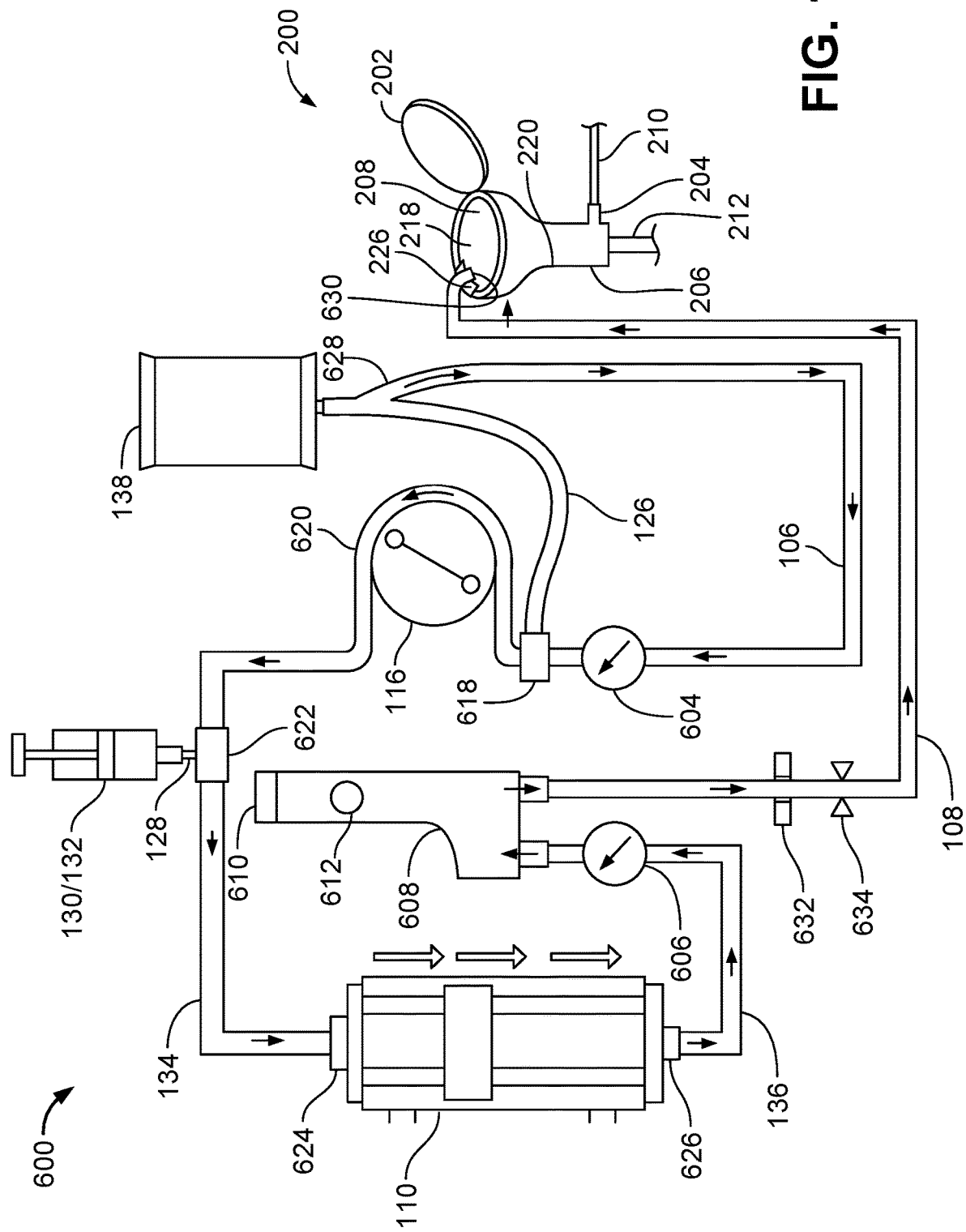
FIG. 16 is a schematic of a blood circuit and drain apparatus of the hemodialysis system of FIG. 1.

Referring to FIGS. 5 and 16, a method of preparing the hemodialysis system 100 for hemodialysis treatment will now be described. Before hemodialysis treatment is initiated, the blood component set 104 is connected to the hemodialysis machine 102, as shown in FIG. 1. For example, a first end of the arterial patient line 106 is attached to the pump line 620 via the first pump line adaptor 618 and a first end of the venous patient line 108 is attached to an exit port of the air release device 608. Further, as depicted in FIG. 16, before priming the hemodialysis system 100, a patient end 628 of the arterial patient line 106 is coupled to the saline bag 138 via the saline delivery line 126 and a patient end 630 of the venous patient line 108 is attached to the drain apparatus 200 using the clip 226 of the drain apparatus. By attaching the venous patient line 108 to the drain apparatus 200 using the clip 226, the patient end 630 of the venous patient line 108 can be positioned within the chamber 208 of the drain apparatus 200 without touching the walls of the inner funnel 218 of the drain apparatus 200

To begin priming the system 100, saline is introduced from the saline bag 138 into the blood circuit 600 via the arterial patient line 106. To draw the saline from the saline bag 138 through the arterial patient line 106 and into the blood circuit 600, the blood pump 132 is turned on. The blood pump 132 draws the saline from the saline bag 138, through saline delivery line 126 and the arterial patient line 106, through the arterial pressure sensor 604, and through the pump line 602 towards the dialyzer 110. The saline flows into the dialyzer 110 via the dialyzer inlet line 134 and exits the dialyzer 110 via the dialyzer outlet line 136. As the saline flows through the dialyzer outlet line 136 towards the air release device 608, the saline passes through the venous pressure sensor 606.

Next, the saline flows through an entry port of the air release device 608 and fills the air release device 608. To fill the air release device 608, the venous patient line 108, which leads away from the air release device 608, is clamped while the saline is forced into the air release device 608. Air is forced out the top of the air release device 608 and through the vent assembly 610 as saline fills the air release device. Because the venous patient line 108 is still clamped at this time, the operation of the blood pump 116 builds a substantial amount of pressure within the blood air release device 608 via the vent assembly 610 of the air release device 608. The saline does not pass through the vent assembly 610 because the membrane of the vent assembly 610 is hydrophobic.

Once the air release device 608 is filled with saline, the clamp is removed from the venous patient line 108 and saline flows through the venous patient line 108 towards the patient end 630 of the venous patient line 108. Once the entire blood circuit 600 is filled with saline, any additional (e.g., excess) saline pumped through the blood component set 104 exits the patient end 630 of the venous patient line 108 and is captured by the chamber 208 of the drain apparatus 200. The drain apparatus outlet valve 216 fluidly connected to the outlet line 212 of the drain apparatus 200 is open and the drain apparatus pump 214 is turned on during priming to draw saline collected from the venous patient line 108 by the drain apparatus 200 to the drain line 112 via the outlet line 212.

The process of priming described above functions to remove air from within the blood circuit 600 and fills the blood circuit 600 with saline from the patient end 628 of the arterial patient line 106 to the patient end 630 of the venous patient line 108. Once all air is out of the patient lines 106, 108 and the blood circuit 600 is filled with saline, clamps are closed on the patient ends 628, 630 of the patient lines 106, 108. Once clamped, the patient end 628 of the arterial patient line 106 is removed from the saline bag 138 and the patient end 630 of the venous patient line 108 is removed from the drain apparatus 200.

After the initial priming, the patient ends 628, 630 of the patient lines 106, 108 can be connected together using a sterile recirculation connector and the saline contained within the blood circuit 600 can be recirculated through the blood circuit 600 away from the drain apparatus 200 until the patient 602 is ready for treatment.

Once the blood circuit 600 has been primed and the patient 602 is ready for treatment, the patient ends 628, 630 of the arterial and venous patient lines 106, 108 are connected to a patient 602, as shown in FIG. 6, and hemodialysis is initiated. Referring to FIGS. 5 and 6, a method of performing dialysis treatment using the hemodialysis system 100 will now be described.

During hemodialysis, blood is circulated through the blood circuit (i.e., the various blood lines and blood components, including the dialyzer 110, of the blood component set 104). At the same time, dialysate is circulated through the dialysate circuit (i.e., the various fluid lines and dialysate components, including the dialyzer 110).

As shown in FIG. 5, dialysate is generated by the dialysate circuit 500 and provided to the dialyzer 110 via fluid line of the dialysate circuit 500. For example, referring to FIG. 5, during hemodialysis, recirculation valve 508 is closed and water inlet valve 510 is open, and water used for generating dialysate is received by the hydraulic circuit 500 through the water inlet port 502. The water passes through the heat exchanger 506, the open water inlet valve 510, and into the heating and deaeration chamber 512. In some implementations, if the temperature of the water as detected by temperature control thermistor 514 of the heating sub-chamber 512A is below a threshold temperature, a heater 516 in heating sub-chamber 512B can be used to heat the water above the threshold temperature. The heated water passes through an aeration orifice 518 positioned between sub-chambers 512C, 512D to deaerate the flow of water.

During hemodialysis, the deaeration pump 520 pumps the flow of heated and deaerated water from deaeration and heating chambers 512 to the mixing chambers 534, 536 via a fluid line. The flow of heated and deaerated water combines with a flow of acid concentrate provided by the acid concentrate pump 526 and a flow of bicarbonate provided by the bicarbonate pump 532. As shown in FIG. 5, the acid concentrate can be filtered by acid concentrate filter 524 prior to introduction of the concentrate into the flow of heated water. Similarly, bicarbonate provided by bicarbonate pump 532 can be filtered by bicarbonate filter 530 prior to introduction of the bicarbonate into the flow of heated water. The mixing chambers 534, 536 receive the combined flow of heated water, acid concentrate, and bicarbonate and mix the fluids to generate a uniform dialysate fluid.

As previously discussed, the dialysate flows from mixing chamber 536 to the first chamber half 558, 560 of one of the balancing devices 554, 556 as controlled by valves 538 and 542, respectively. As previously discussed, as fresh dialysate is flowing into one balancing device 554, spent dialysate is flowing into the other balancing device 556, and vice versa. As fresh dialysate flows into a first chamber halves 558, 560, spent dialysate is forced out the respective second chamber halves 562, 564 through valves 548, 552 via drain line 112.

Additionally, as spent dialysate flows into the second chamber halves 562, 564 from dialyzer 110 via the air separation chamber 593, the fresh dialysate in the respective first chamber halves 558, 560 is forced out the respective balancing devices 554, 556 through valves 546, 550, respectively, towards the dialyzer 110.

Before the dialysate generated by the dialysate circuit 500 is provided to the dialyzer 110, the dialysate passes through the dialysate filter 574 to remove any potential impurities in the dialysate. During hemodialysis, bypass valve 575 is closed and dialyzer inlet valve 576 is open to direct flow of dialysate from the dialysis filter 574 to the dialyzer 110, and dialysate flows from the dialysate filter 574 to the dialyzer 110. In addition, during hemodialysis, drain apparatus inlet valve 242 is closed to prevent dialysate from flowing into the drain apparatus during dialysis. If, during hemodialysis, pressure transducer 240 detects a build-up of fluid in the drain apparatus 200 for any reason (e.g., malfunction of valve 242), control valve 216 can be opened to empty the drain apparatus without interrupting the hemodialysis. In some implementations, the dialysate flows through a dialysate flow line indicator 578 prior to entering the dialyzer 110.

During hemodialysis, spent dialysate exits the dialyzer 110 and passes through the dialysate circuit via the drain line 112. As depicted in FIG. 5, during hemodialysis, the dialyzer outlet valve 584 is open and spent dialysate is received from the dialyzer 110 by the drain line 112 and passes through a fluid line filter 582 and dialyzer outlet valve 584. Fluid line filter 582 filters the spent dialysate exiting the dialyzer 110. The spent dialysate exiting the dialyzer 110 passes through a pressure sensor 586 configured to measure the pressure of dialysate entering the drain line 112 from the dialyzer 110 and passes through a blood leak detector 588 configured to detect whether blood has leaked into the dialysate across the dialyzer 110 membrane.

Before entering the air separation chamber 593, the spent dialysate flows through a post-dialyzer temperature thermistor 590 and a post-dialyzer conductivity cell 592 configured to regulate the temperature of the spent dialysate.

As previously discussed, the spent dialysate is received by the air separation chamber 593, which is configured to vent off any air contained in the dialysate through valve 594. The dialysate flow pump 595 draws dialysate from the air separation chamber 593, through a drain check valve 596, and into one of the second chamber halves 562, 564 of the balancing devices 554, 556 through one of valves 540 and 544, respectively. Drain check valve 596 is fluidly coupled to the drain line 112 downstream of the dialysate flow pump 595 and is configured to prevent fluid from flowing backwards along the drain line 112 towards the dialysate flow pump 595.

As fresh dialysate is provided to one of the first chamber halves 558, 560 of the balancing devices 554, 556, the spent dialysate in the respective second chamber half is forced out the respective balancing device 554, 556 along the drain line 112 to the heat exchanger 506.

During hemodialysis, the ultrafiltration pump 597 operates simultaneously with the dialysate flow pump 595 to generate an increased vacuum pressure within the drain line 112 connecting the air separation chamber 593 to the dialyzer 110, and thus creates increased vacuum pressure within the dialyzer 110. As a result of this increased vacuum pressure, additional fluid is pulled from the blood circuit 600 into the dialysate circuit 500 across the semi-permeable structure (e.g., semi-permeable membrane or semi-permeable microtubes) of the dialyzer 110. This additional fluid is passed along the drain line 112 through an ultrafiltration pump filter 598 downstream of the air separation chamber 593 and through an ultrafiltration check valve 599, and to the drain line 112 and the heater. The ultrafiltration check valve 599 prevents fluid from flowing backwards along the ultrafiltration line 591 towards the ultrafiltration pump 597.

After passing through the heat exchanger 506, spent dialysate exits the dialysate circuit through the drain line 112 and travels to a drain outside the hemodialysis machine 102.

Referring to FIG. 6, during hemodialysis, the patient's 602 blood is drawn from the patient end 628 of the arterial patient line 106 into the blood circuit 600 by the blood pump 116. In some implementations, prior to providing the patient's 602 blood the dialyzer 110, the flow of blood is combined with saline provided by saline delivery line 126 and one or more drugs (e.g., heparin) provided from syringe 130 by drug pump 132 through the drug delivery line 128. The combined flow enters the dialyzer 110 through dialyzer inlet line 134.

After passing through the dialyzer 110, the patient's 602 filtered blood exits the dialyzer 110 and enters the blood circuit 600 through the dialyzer outlet line 136. The blood flows through the venous pressure sensor 606 to the air release device 608. As previously discussed, the air release device 608 removes any air contained within the filtered blood through the vent assemble 610.

After flowing through the air release device 608, the deaerated, filtered blood flows through the venous patient line 108 to an air bubble detector 632. As previously discussed, the air bubble detector is configured to detect air bubbles contained in the flow of blood. After passing through the air bubble detector 632, the filtered blood passes through an occluder 634. As previously discussed, the occluder 634 can, for example, be connected to the air bubble detector 632 so that the occluder 634 can be activated when the air bubble detector 632 detects an air bubble within the venous patient line 108. If no air bubbles are detected by the air bubble detector 632, the blood flows through the occluder 634 to the patient end 630 of the venous patient line 108, and into the patient.

After the dialysis treatment has been performed, blood contained within the blood circuit 600 is reinfused (i.e. rinsed back) to the patient 602. To perform reinfusion, the arterial patient line 106 is clamped, and the patient end 628 of the arterial patient line 106 is attached to the saline bag 138. The arterial patient line 106 is then unclamped, and saline is pumped from the saline bag 138 through the arterial patient line 106 by the blood pump 116. The saline is then pumped throughout the entire blood circuit 600 to the patient end 630 of the venous patient line 108 to push any blood remaining in the blood circuit 600 back to the patient 602 and fill the circuit 600 with saline.

Once a desired amount of the blood contained within the blood circuit 600 has been reinfused back to the patient 602, the patient lines 106, 108 are clamped and the venous patient line 108 is removed from the patient 602. As depicted in FIG. 16, the patient end 630 of the venous patient line 108 is attached to the drain apparatus 200 using the clip 226. By attaching the venous patient line 108 to the drain apparatus 200 using the clip 226, the patient end 630 of the venous patient line 108 is positioned within the chamber 208 of the drain apparatus 200 without touching the walls of the inner funnel 218. The blood pump 132 draws the saline from the saline bag 138 through the arterial patient line 106 and circulates the saline throughout all components of the blood circuit 600. After circulating through the blood circuit 600, the saline exits the patient end 630 of the venous patient line 108 and collects in the chamber 208 of the drain apparatus 200. The drain apparatus outlet valve 216 is open and the drain apparatus pump 214 is turned on to draw the saline collected from the venous patient line 108 by the drain apparatus 200 to the drain line 112 via the outlet line 212. Saline is continuously pumped through the blood circuit 600 until all remaining patient fluids have been flushed from the blood circuit 600 into the drain apparatus 200. In some cases, for example, saline is pumped through the blood circuit 600 until the saline bag 138 is empty.

After completing the patient's treatment and flushing the blood circuit 600, the blood component set 104 is disconnected from the module 114 of the hemodialysis machine 102 and discarded. Dialysate contained within the dialysate circuit is pumped to a drain outside the hemodialysis machine via the drain line 112 using the dialysate flow pump 212 and/or the ultrafiltration pump 214. Following treatment, the dialysate circuit and drain apparatus are disinfected in preparation for a subsequent treatment.

Referring to FIGS. 2 and 5, a method of disinfecting the dialysate circuit 500 and drain apparatus 200 will now be described. As previously discussed, after completing dialysis treatment and flushing the blood circuit 600, the venous patient line 108 is removed from the drain apparatus 200 and discarded with the rest of the blood component set 104. In some implementations, during disinfection, one or more of the acid concentrate port 522 and bicarbonate port 528 of the dialysate circuit are removed from the acid concentrate and bicarbonate sources and are connected to a source of chemical disinfectant fluid concentrate. Prior to disinfection of the dialysate circuit 500 and the drain apparatus 200, the lid 202 of the drain apparatus 200 is closed to form a liquid-tight seal with the chamber 208 of the drain apparatus 200 and the drain apparatus outlet valve 216 on the outlet line 212 is closed.

Once the lid 202 of the drain apparatus is closed and the drain apparatus outlet valve 216 is closed, sterilization of the dialysate circuit 500 and drain apparatus 200 may begin. To disinfect the dialysate circuit 500 and drain apparatus 200, water is pumped into the dialysate circuit 200 from the water inlet port 502 to the heat exchanger 506.

Water heated by heat exchanger 506 flows from the heat exchanger 506 through the recirculation valve 508 to the heating and deaeration chamber 512. The deaeration and heating chamber 512 is configured to heat and deaerate water received by the dialysate circuit 500 through the water port 502 for disinfection. The water is heated to a desired temperature in the heating and deaeration chamber 512.

One or more of the acid concentrate pump 526 and the bicarbonate pump 532 pump chemical disinfectant concentrate into the flow of heated water exiting the heating and deaeration chamber 512. The combined flow of heated water and chemical disinfectant concentrate are provided to the mixing chambers 534, 536 to mix the heated water and disinfectant concentrate to create a homogenous disinfectant fluid.

Disinfectant fluid exits mixing chamber 536 and flows through valves 538 and 542 to the one of the first chamber halves 558, 560 of the one of the balancing devices 554, 556. As with the flow dialysate solution, as disinfectant fluid flows through the first chamber half 558 of one balancing device 554, disinfectant fluid flows into the second chamber half 564 of the other balancing device 556, and vice versa, as controlled by valves 538 through 552. Further, as with the flow of dialysate solution, as disinfectant fluid flows into the first chamber halves 558, 560 of the balancing devices 554, 556, disinfectant fluid is simultaneously forced out of the second chamber halves 562, 564, and vice versa.

The disinfectant fluid flowing out of the first chamber halves 558, 560 of the balancing devices 554, 556 flows through a conductivity cell 570 and a temperature monitor thermistor 572 towards the dialysate filter 574. During the initial flow of disinfectant fluid through the dialysate circuit 500, the bypass valve 575 is open and the drain apparatus inlet valve 242 and the vent valve 594 are closed to direct disinfectant fluid from the dialysate filter 574 towards the post-dialyzer temperature thermistor 590 and the post-dialyzer conductivity cell 592 and through the air separation chamber 593.

Disinfectant fluid is then pumped from the air separation chamber 593 to one of the second chamber halves 562, 564 of one of the balancing devices 554, 556 through valves 540 and 544, respectively, by one or more of the dialysate flow pump 595 and the ultrafiltration pump 597. As disinfectant fluid flows into the first chamber halves 558, 560, the disinfectant fluid in the second chamber halves 562, 564 flows out of the second chamber halves 562, 564 through valves 548, 552, respectively via the drain line 112. During disinfection, the drain valve 589 is closed, and disinfectant fluid exiting second chamber halves 562, 564 flows through the drain line 112 to the heat exchanger 506 and then back down through recirculation valve 508 via a fluid line.

Water is continuously added the dialysate circuit 500 via water inlet port 502 in order to produce disinfectant fluid to circulate throughout the entire dialysate circuit 500. During disinfection, water inlet pressure regulator 504 monitors the fluid pressure of the fluid line extending from the water inlet 502, and whenever the water inlet pressure regulator 504 detects that a threshold pressure indicating the entire dialysate circuit is filled with disinfectant fluid has been reached, bypass valve 575 is closed and drain apparatus inlet valve 242 is opened. By closing bypass valve 575 and opening drain apparatus inlet valve 242, disinfectant fluid exiting the dialysate filter 574 is directed to the drain apparatus 200 via the inlet line 210 coupled to the outlet of the dialysate filter 574.

Still referring to FIGS. 2 and 5, disinfectant fluid flows through the open drain apparatus inlet valve 242 and the inlet line 210 to the inlet port 204 of the drain apparatus 200, and flows up into and fills the annular channel 228 between the inner funnel 218 and outer funnel 220. Once the disinfectant fluid reaches the top of the annular channel 228, the curved upper lip 222 of the outer funnel 220 forces the solution over the annular surface 224 of the inner funnel 218, causing the disinfectant fluid to run down the surface of the inner funnel 218. Because the annular channel 228 completely surrounds the inner funnel, the disinfectant fluid is evenly distributed across the surface of the inner funnel 218 and washes the entire surface of the inner funnel 218.

During this portion of the disinfection, the drain apparatus outlet valve 216 is closed to allow the chamber 208 of the drain apparatus 200 to be filled with disinfectant fluid. In addition, during this portion of disinfection, the pump 214 is in a position to prevent disinfectant fluid from flowing to the drain line 112 via the outlet line 212 in order to allow the chamber 208 of the drain apparatus 200 to be filled with disinfectant fluid. As disinfectant fluid enters the chamber 208 of the drain apparatus 200 via the inlet line 210 and annular channel 228, the chamber 208 begins to fill with disinfectant fluid and any air in the chamber 208 exits out the vent 230 and hydrophobic filter 232 coupled to the closed lid 202 of the drain apparatus 200. The hydrophobic filter 232 attached to and covering the vent 230 prevents disinfectant fluid from passing through the vent 232. This arrangement of the vent 230 and hydrophobic filter 232 allows substantially all of the air in the chamber 208 to be displaced by disinfectant fluid, allowing for almost the entire chamber 208 of the drain apparatus 200 to be filled with disinfectant fluid when the outlet valve 216 is closed.

The pressure sensor 240 coupled to the outlet line 212 of the drain apparatus 200 monitors the fluid pressure in the chamber 208 during disinfection. Once the pressure sensor 240 detects that the pressure in the chamber 208 has reached a threshold pressure indicating that the chamber 208 is filled with fluid, drain apparatus inlet valve 242 is closed to prevent any additional disinfectant fluid from entering the chamber 208 via the inlet line 210. In some implementations, once the pressure sensor 240 detects that the pressure in the chamber 208 has reached a threshold pressure indicating that the chamber 208 is filled with fluid, a signal is sent to close the water inlet valve 510 in order to prevent additional water from being added to the dialysis circuit 500 via the water inlet port 502 and stop the production of disinfectant fluid.

Once the chamber 208 is full of disinfectant fluid, the drain apparatus outlet valve 216 remains closed for a predetermined amount of time to allow the disinfectant fluid to dwell in the chamber 208 for a predetermined amount of time. In some implementations, the disinfectant fluid dwells in the chamber 208 for at least 10 minutes (e.g. at least 30 minutes, 10 minutes to 60 minutes).

After the disinfectant fluid has dwelled in the chamber 208 for the predetermined amount of time, the drain apparatus outlet valve 216 is opened. The drain apparatus pump 214 draws the disinfectant fluid out of the chamber 208 through outlet port 206 and the open drain apparatus outlet valve 216 to the drain line 112 via the outlet line 212. The drain apparatus pump 214 continues to run until all of the disinfectant fluid is pumped out of the drain apparatus 200 to the drain line 112.

Similarly, once the disinfectant fluid has recirculated through the dialysate circuit for a predetermined amount of time, the recirculation valve 508 is closed and the drain valve 589 is opened to direct the disinfectant fluid through the drain line 112 towards a drain. In some implementations, the dialysate flow circuit pumps the disinfectant fluid through the balancing devices 554, 556 and along the drain line 112 through drain valve 589. In some implementations, the drain valve 589 and the drain apparatus outlet valve 216 are opened at or near the same time, and the dialysate circuit 500 and drain apparatus 200 are drained of disinfectant fluid simultaneously.

While certain embodiments have been described above, other embodiments are possible.

Figure 7:
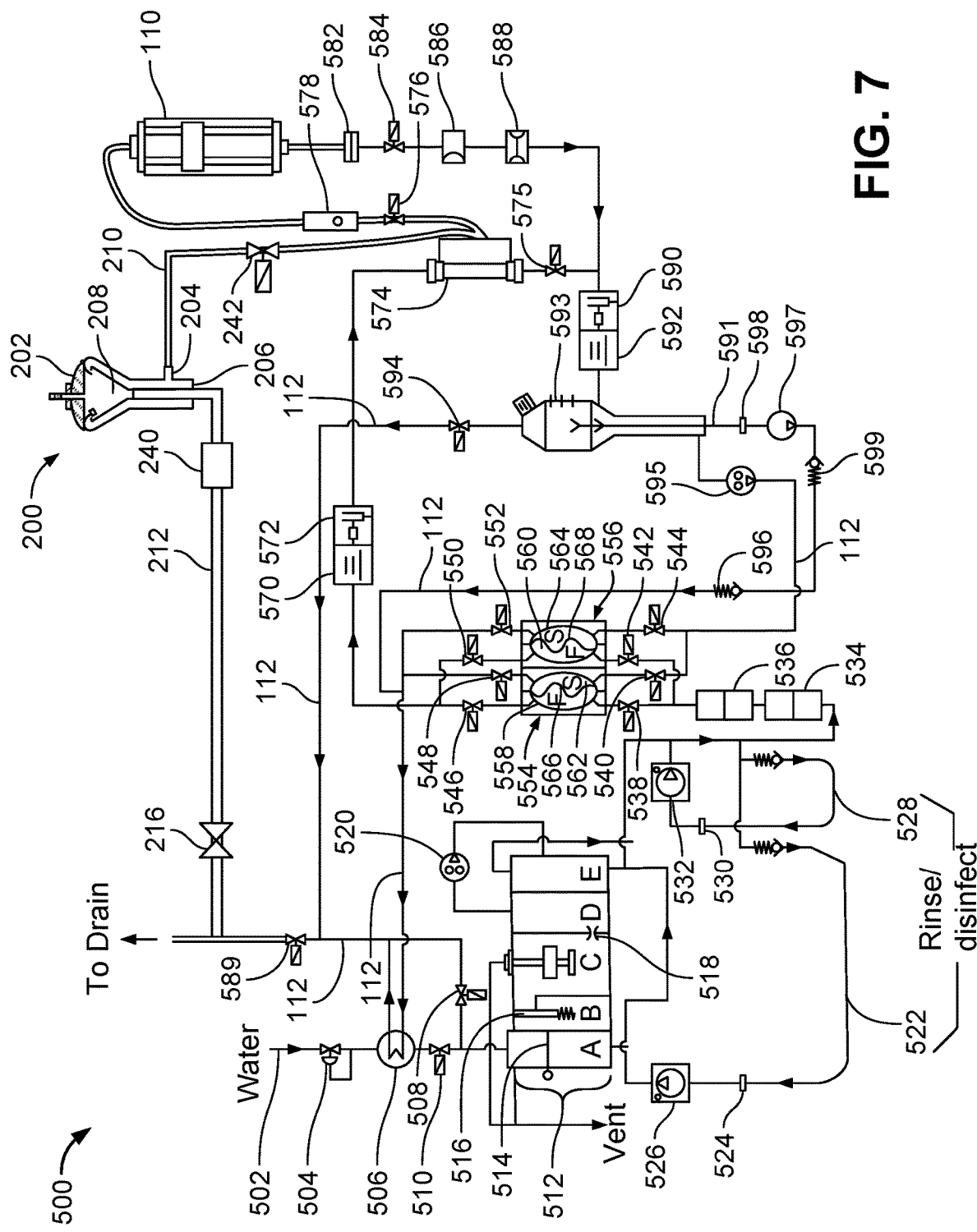
FIG. 7 is a schematic of the dialysate circuit of FIG. 5 with an alternate coupling of the drain apparatus to the dialysate circuit.

FIG. 7, for example, is a schematic showing an alternate arrangement of the dialysate circuit 500 and the drain apparatus 200 of the hemodialysis machine 102. As shown in FIG. 7, the drain apparatus 200 does not include a drain apparatus pump (e.g. drain apparatus pump 214 of FIGS. 2-5) along the outlet line 212 between the outlet port 206 of the drain apparatus 200 and the drain line 112. In such instances, drain apparatus 200 is configured such that the fluid contained within the chamber 208 of the drain apparatus 200 is gravity drained to the drain line 112 via the outlet line 212 whenever the drain apparatus valve 216 is open. For example, during disinfection of the drain apparatus 200, disinfectant fluid contained in the chamber 208 of the drain apparatus 200 drains through the outlet line 212 to the drain line 112 by gravity whenever the drain apparatus outlet valve 216 is opened.

In some embodiments, the drain apparatus includes a drain pump along the outlet line 210 (such as drain pump 214), but does not include a drain valve (e.g., drain valve 216 of FIGS. 2-5, 7) along the outlet line 212 between the outlet port 206 of the drain apparatus 200 and the drain line 112. In such instances, drain pump 214 acts to control the flow of fluid out of the chamber 208 via the outlet line 212. For example, during disinfection of the drain apparatus 200, the drain pump 214 can be configured to block fluid from flowing through the outlet line 212 to the drain until the pump 214 is activated to pump the fluid from the chamber 208 to the drain line 112 via the outlet line 212.

Figure 8:
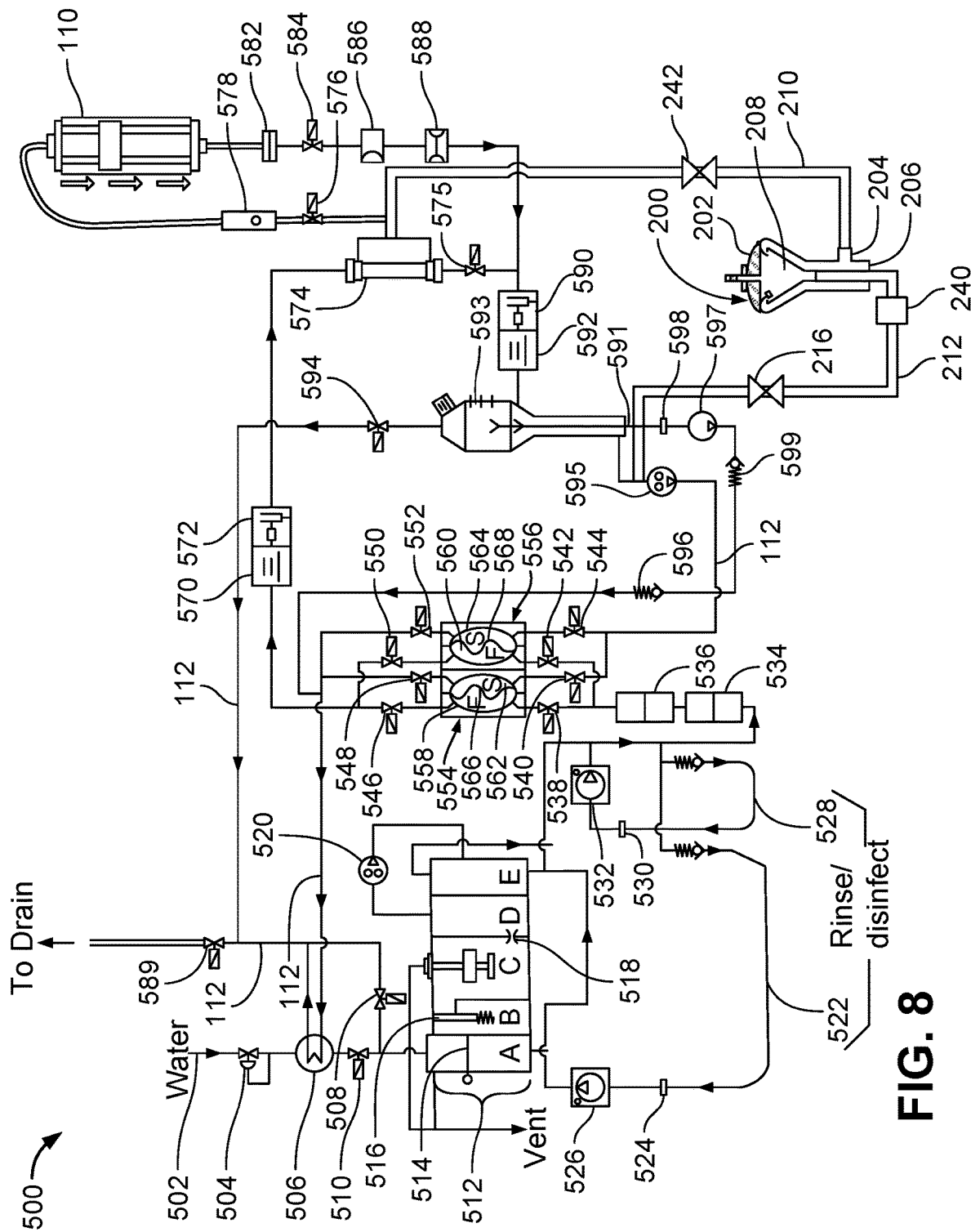
FIG. 8 is a schematic of the dialysate circuit of FIG. 5 with an alternate coupling of the drain apparatus to the dialysate circuit.

FIG. 8 is a schematic showing an alternate arrangement of the dialysate circuit 500 and drain apparatus 200 of the hemodialysis machine 102. As shown in FIG. 8, the inlet line 210 of the drain apparatus 200 is fluidly connected to the fluid line downstream of the dialysate filter 574 and the outlet line 212 of the drain apparatus 200 is fluidly connected to a portion of the drain line 112 of the dialysate circuit 500 upstream of the dialysate flow pump 595. In this arrangement, as depicted in FIG. 8, the drain apparatus 200 does not include a drain apparatus pump (e.g. drain apparatus pump 214 of FIGS. 2-5) along the outlet line 212. Instead, the negative pressure created by dialysate flow pump 595 of the dialysate circuit 500 is used to draw fluid contained within the chamber 208 of the drain apparatus 200 out of the drain apparatus 200 through the drain apparatus outlet valve 216 via the outlet line 212. Using this arrangement, fluid contained within the chamber 208 of the drain apparatus 200 is drained through the outlet line 212 and provided to the dialysate circuit 500 downstream of the air separation chamber 593. The dialysate flow pump 595 is then used to pump the fluid away from the drain apparatus 200 through the drain line 112 to one of the second chamber halves 562, 564 of one of the balancing devices 554, 556 and on to the drain, as described above. For example, using this arrangement during disinfection of the drain apparatus 200, the drain apparatus outlet valve 216 is open and the dialysate flow pump 595 draws the disinfectant fluid contained in the chamber 208 of the drain apparatus 200 through the outlet line 212 to a portion of the drain line 112 of the dialysate circuit 500 downstream of the air separation chamber 593. The dialysate flow pump 595 then flows the disinfectant fluid to one of the second chamber halves 562, 564 of one of the balancing devices 554, 556 via the drain line 112. Finally, the disinfectant fluid exits the second chamber halves 562, 564 of the balancing devices 554, 556 and flows to a drain via the drain line 112.

Similarly, in some implementations, the outlet line 212 of the drain apparatus 200 can be fluidly connected to a portion of the drain line 112 of the dialysate circuit 500 upstream of the ultrafiltration pump 597 of the dialysate circuit. In this arrangement, negative pressure created by ultrafiltration pump 597 of the dialysate circuit 500 is used to draw fluid contained within the chamber 208 of the drain apparatus 200 out of the drain apparatus 200 through the drain apparatus outlet valve 216 via the outlet line 212. The ultrafiltration pump 597 is then used to pump the fluid away from the drain apparatus 200 through the drain line 112 to one of the second chamber halves 562, 564 of the one of balancing devices 554, 556 and on to the drain, as described above.

Additionally, while the inlet line 210 of the drain apparatus 200 has been described as being fluidly connected to the fluid line 108 downstream of the dialysate filter 574, the inlet line 210 can alternatively be coupled to a fluid line of the dialysate circuit 500 at any other point within the dialysate circuit 500 upstream of the dialyzer 110.

While the drain apparatus 200 is described as having a vent 230 and hydrophobic filter 232 to allow for complete filling of the chamber 208 of the drain apparatus 200, other configurations of the drain apparatus may alternatively be provided to allow for complete filling of the chamber 208. FIGS. 9-14 depict cross-section views of alternate drain apparatuses for the hemodialysis system of FIG. 1.

Figure 9:
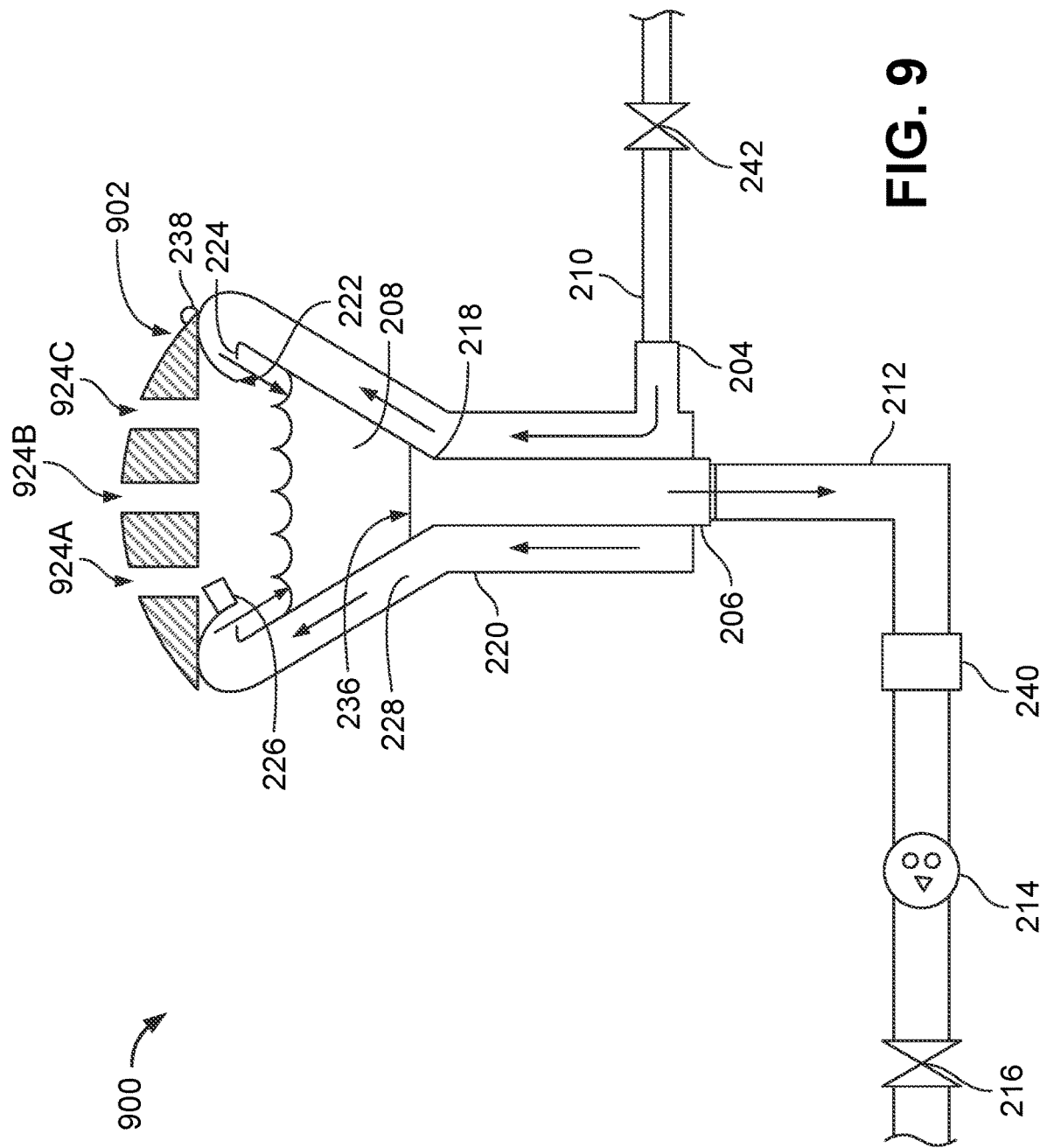
FIGS. 9-15 are cross-section views of alternate drain apparatuses for the hemodialysis system of FIG. 1.

As depicted in FIG. 9, in some implementations, rather than having a vent and hydrophobic filter (e.g., vent 230 and hydrophobic filter 232 of FIG. 2), the lid 902 of the drain apparatus can include a plurality of vents or holes 924 through the lid 902. In this arrangement, the lid 902 of the drain apparatus 900 is liquid-tight when closed and fluid contained within the chamber 208 of the drain apparatus can exit through the holes 924 in the lid 902. This arrangement of the holes 924 in the lid 902 of the drain apparatus 900 allows all of the air in the chamber 208 of the apparatus 900 to be displaced by disinfectant fluid during disinfection, allowing for the entire chamber 208 to be filled with disinfectant fluid when the outlet valve 216 is closed. In some implementations, in order to fill the chamber 208 of the drain apparatus 900 with disinfectant fluid during disinfection, a pressure sensor 240 coupled to the outlet line 212 monitors the fluid pressure in the chamber 208 of the drain apparatus 900 during disinfection, and once the pressure sensor 240 detects that the pressure in the chamber 208 has reached a threshold pressure indicating that the chamber 208 is filled with fluid, drain apparatus inlet valve 242 is closed to prevent additional disinfectant fluid from entering the chamber 208 via the inlet line 210. Once the chamber 208 is filled with disinfectant fluid, the disinfectant fluid is allowed to dwell in the chamber 208 for a predetermined amount of time. In some implementations, once the pressure sensor 240 detects that the pressure in the chamber 208 has reached a threshold pressure indicating that the chamber 208 is filled with fluid, a signal is sent to close the water inlet valve 510 in order to prevent additional water from being added to the dialysis circuit 500 via the water inlet port 502 and stop the production of disinfectant fluid. After the disinfectant fluid has dwelled in the chamber 208 for the predetermined amount of time, the drain apparatus outlet valve 216 is opened and the drain apparatus pump 214 draws the disinfectant fluid out of the chamber 208 through outlet port 206 and the open drain apparatus outlet valve 216 to the drain line 112 via the outlet line 212.

Figure 10:
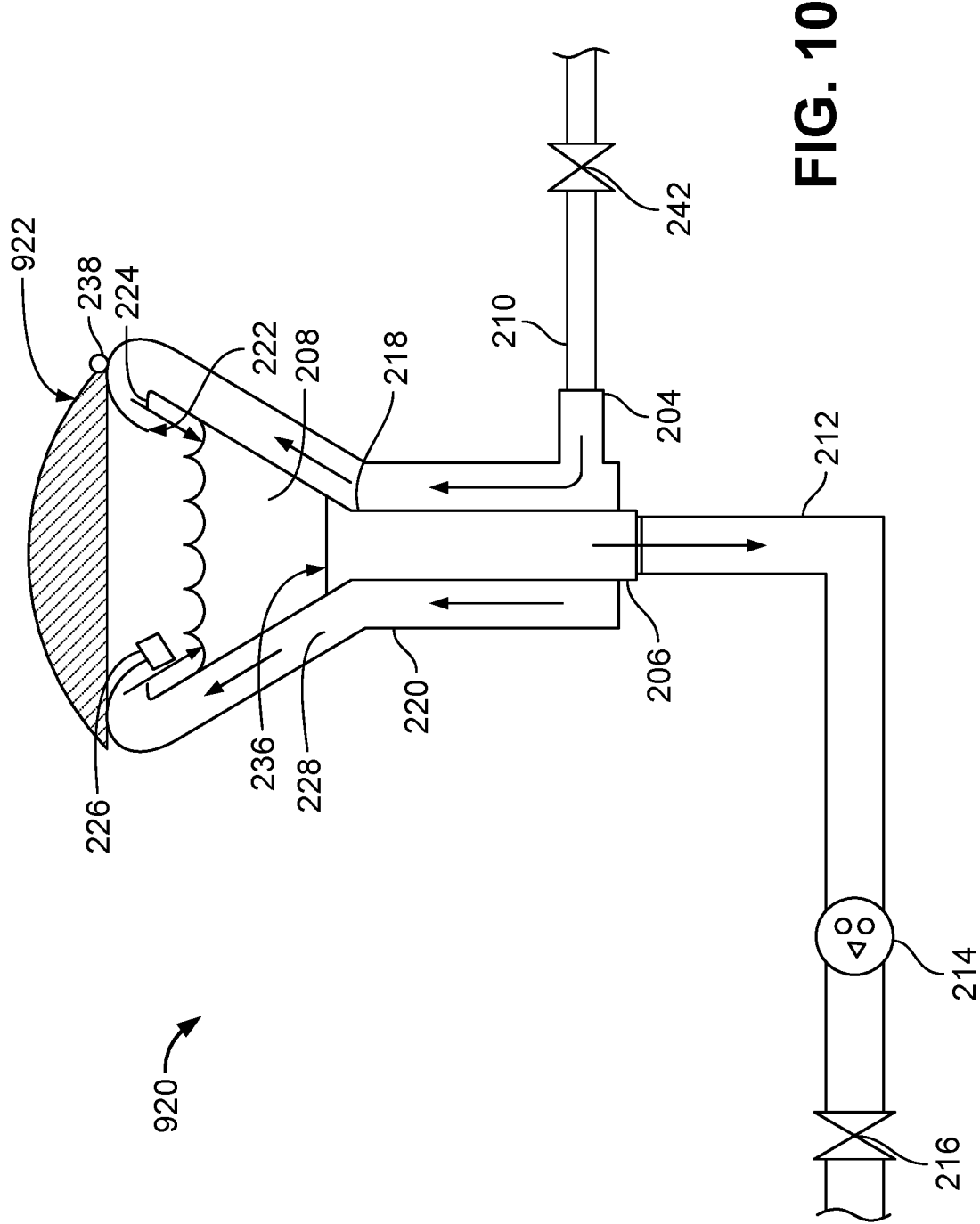

As depicted in FIG. 10, in some implementations, the lid 922 of the drain apparatus 920 is not liquid-tight when in a closed position and the chamber 208 of the drain apparatus 920 is filled with disinfectant fluid during disinfection by metering the flow of disinfectant fluid into inlet line 210 of the drain apparatus 920 using the balancing devices 554, 556 of the dialysate circuit 500. For example, once the drain apparatus inlet valve 242 is opened during disinfection, the amount of disinfectant fluid exiting the balancing devices 554, 556 towards the drain apparatus 920 can be controlled to provide the exact amount of disinfectant fluid required to fill the fluid line between the balancing devices 554, 556 and the inlet line 210, the inlet line 210, and the chamber 208 of the drain apparatus 920. In this arrangement, as disinfectant fluid enters the chamber 208, an equal amount of air contained in the chamber 208 exits the chamber 208 around the non-liquid-tight lid 922. In some implementation, the lid 922 of the drain apparatus 920 includes vents or holes (such as holes 924 of FIG. 9). In some examples, each stroke of the balancing devices 554, 556 provides 30 ccs of disinfectant fluid to the drain apparatus 920 via the inlet line 210, and a calculated number of strokes of the balancing devices 554, 556 are performed in order to provide the amount of disinfectant fluid necessary to fill the chamber 208 of the drain apparatus 920. Once the chamber 208 is filled with disinfectant fluid, drain apparatus outlet valve 216 remains closed to allow the disinfectant fluid to dwell in the chamber 208 for a predetermined amount of time. After the disinfectant fluid has dwelled in the chamber 208 for the predetermined amount of time, the drain apparatus outlet valve 216 is opened and the drain apparatus pump 214 draws the disinfectant fluid out of the chamber 208 through outlet port 206 and the open drain apparatus outlet valve 216 to the drain line 112 via the outlet line 212.

Figure 11:
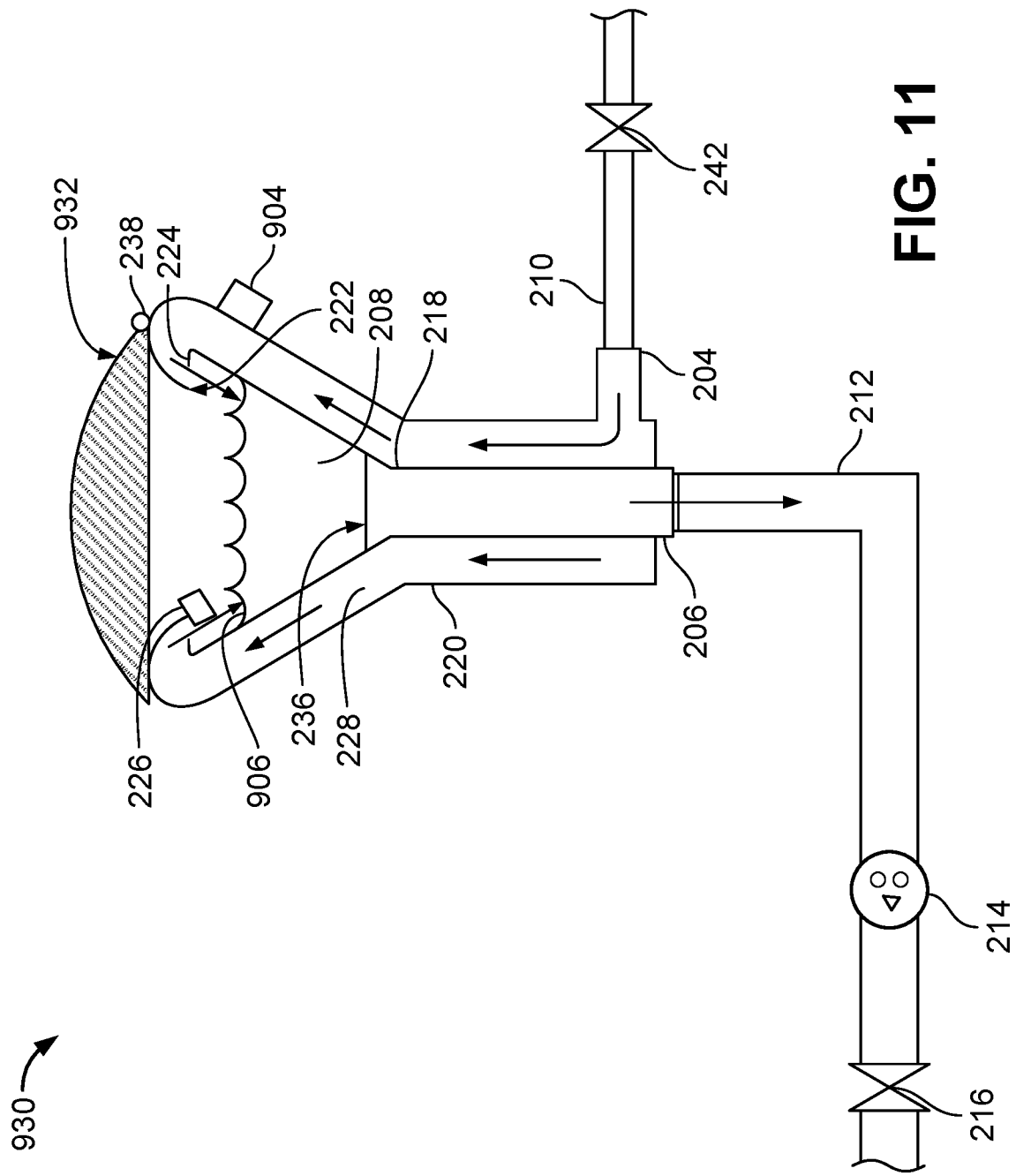

Referring to FIG. 11, in some implementations, the lid 932 of the drain apparatus 930 is not liquid-tight when in a closed position and the drain apparatus 932 includes an ultrasound sensor 904 coupled to the outer funnel 220 is configured to detect the liquid level 906 inside the chamber 208 of the drain apparatus 930. For example, during disinfection, the level of disinfectant fluid in the chamber 208 of the drain apparatus 930 is monitored by the ultrasound sensor 904. During disinfection, drain apparatus outlet valve 216 is closed and disinfectant fluid is provided to the chamber 208 of the drain apparatus 930 via the inlet line 210. In this arrangement, as disinfectant fluid enters the chamber 208, an equal amount of air contained in the chamber 208 exits the chamber 208 around the non-liquid-tight lid 932. In some implementation, the lid 932 of the drain apparatus 930 includes vents or holes (such as holes 924 of FIG. 9). Once the ultrasound sensor 904 detects that level 906 of disinfectant fluid is at or near the top of the chamber 208, the drain apparatus valve 242 is closed to prevent any additional disinfectant fluid from entering the chamber 208 of the drain apparatus 930 and the disinfectant fluid is allowed to dwell in the chamber 208 for a predetermined amount of time. In some implementations, once the ultrasound sensor 904 detects that the liquid level 906 is at or near the top of the chamber 208 such that the chamber 208 is filled with fluid, a signal is sent to close the water inlet valve 510 in order to prevent additional water from being added to the dialysis circuit 500 via the water inlet port 502 and stop the production of disinfectant fluid. After the disinfectant fluid has dwelled in the chamber 208 for the predetermined amount of time, the drain apparatus outlet valve 216 is opened and the drain apparatus pump 214 draws the disinfectant fluid out of the chamber 208 through outlet port 206 and the open drain apparatus outlet valve 216 to the drain line 112 via the outlet line 212.

Figure 12:
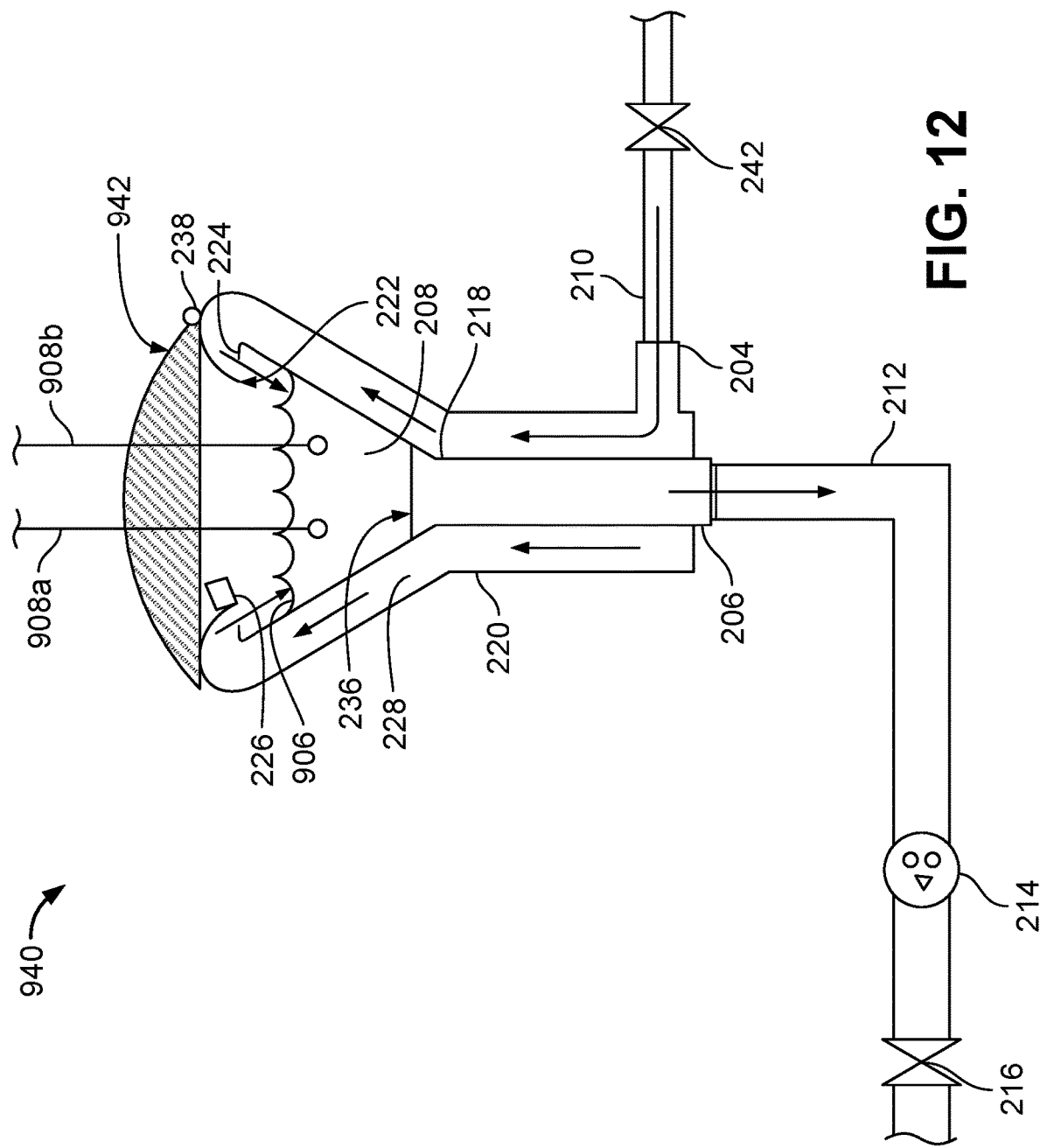

Referring to FIG. 12, in some implementations, the lid 942 of the drain apparatus 940 is not liquid-tight when in a closed position and one or more electrodes 908 are positioned within the chamber 208 of the drain apparatus and configured to detect the level of chemical disinfectant fluid 906 inside the chamber 208 of the drain apparatus 940. For example, the one or more electrodes 908 may be attached to the top of the inner funnel 218 of the drain apparatus and configured to interact with disinfectant fluid. During disinfection, drain apparatus outlet valve 216 is closed and disinfectant fluid is provided to the chamber 208 of the drain apparatus 940 via the inlet line 210. In this arrangement, as disinfectant fluid enters the chamber 208, an equal amount of air contained in the chamber 208 exits the chamber 208 around the non-liquid-tight lid 942. In some implementation, the lid 942 of the drain apparatus 940 includes vents or holes (such as holes 924 of FIG. 9). Once the chemical disinfectant fluid is at or near the top of the chamber 208, the chemicals in the disinfectant fluid will interact with the one or more electrodes 908 located near the top of the chamber 208, indicating that the chamber 208 is full of disinfectant fluid. In some implementations, once the one or more electrodes 908 detect that the level 906 of disinfectant fluid is at or near the top of the chamber 208, the drain apparatus valve 242 is closed to prevent any additional disinfectant fluid from entering the chamber 208 of the drain apparatus and the disinfectant fluid is allowed to dwell in the chamber 208 for a predetermined amount of time. In some implementations, once the one or more electrodes 908 detect that the level 906 of disinfectant fluid is at or near the top of the chamber 208, a signal is sent to close the water inlet valve 510 in order to prevent additional water from being added to the dialysis circuit 500 via the water inlet port 502 and stop the production of disinfectant fluid. After the disinfectant fluid has dwelled in the chamber 208 for the predetermined amount of time, the drain apparatus outlet valve 216 is opened and the drain apparatus pump 214 draws the disinfectant fluid out of the chamber 208 through outlet port 206 and the open drain apparatus outlet valve 216 to the drain line 112 via the outlet line 212. Any of various suitable electrodes can be used to detect fluid levels, such as an in-line tube electrode with an optical slot, a conductive rod probe, etc.

Figure 13:
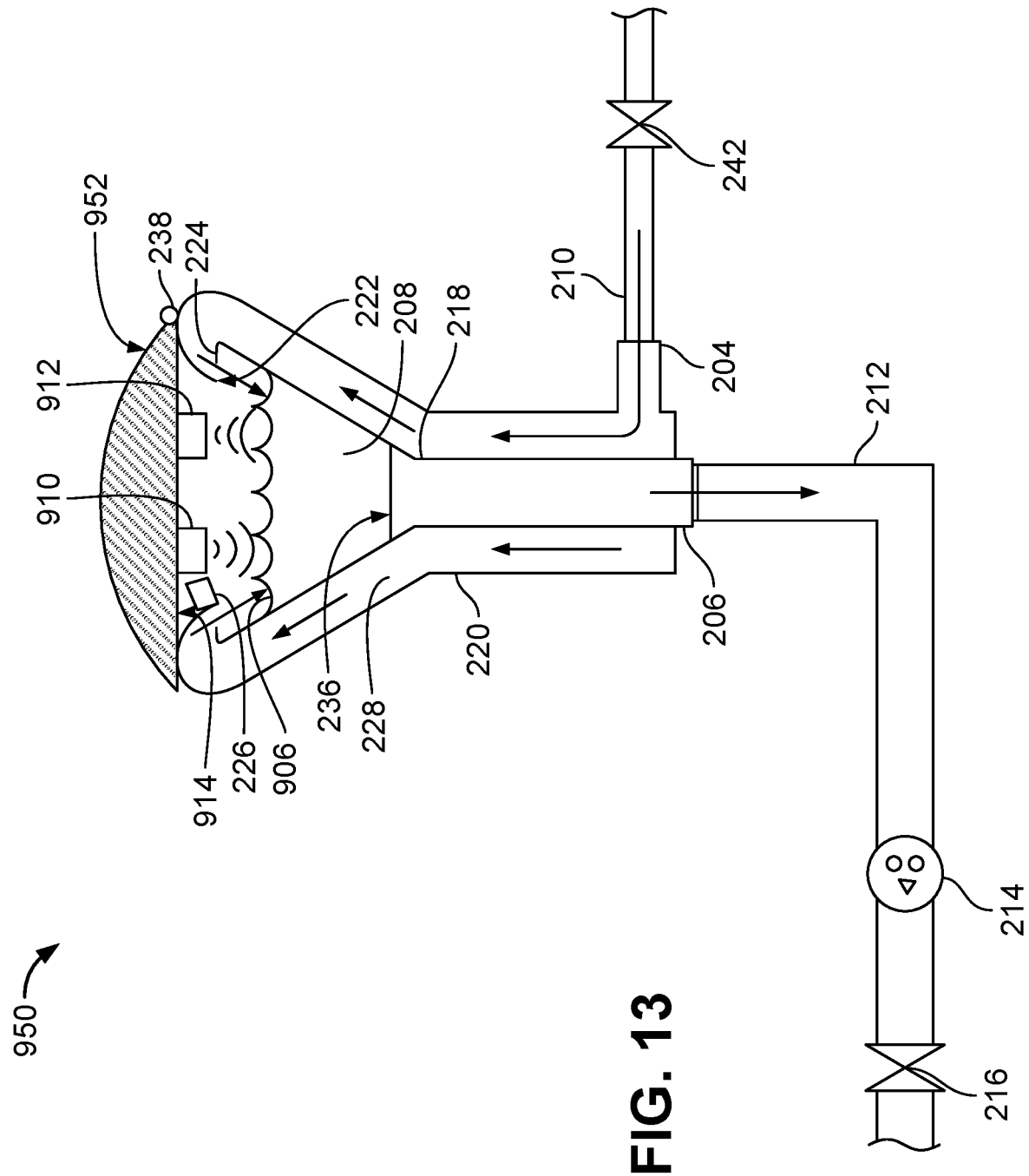

As depicted in FIG. 13, in some implementations, the lid 952 of the drain apparatus 950 is not liquid-tight when in a closed position and the drain apparatus 950 includes an ultrasonic transmitter 910 and ultrasonic receiver 912 configured to detect the liquid level 906 inside the chamber 208 of the drain apparatus 950. In this arrangement, as disinfectant fluid enters the chamber 208, an equal amount of air contained in the chamber 208 exits around the non-liquid-tight lid 958. In some implementation, the lid 952 of the drain apparatus 950 includes vents or holes (such as holes 924 of FIG. 9). As shown in FIG. 13, the ultrasonic transmitter 910 and ultrasonic receiver 912 can be coupled to the inside surface 914 of lid 952 of the drain apparatus 950 facing towards the chamber 208 of the drain apparatus 950 when the lid 952 is in a closed position. During disinfection, drain apparatus outlet valve 216 is closed, lid 950 is closed over the chamber 208, disinfectant fluid is provided to the chamber 208 of the drain apparatus 950 via the inlet line 210, and the ultrasonic transmitter 910 transmits soundwaves through the lid 952 to the chamber 208. The soundwaves transmitted by ultrasonic transmitter 910 bounce off the surface of liquid in the chamber 208 and are received by the ultrasonic receiver 912. Based on the intensity of the soundwaves received by the ultrasonic receiver 912, the level 906 of disinfectant fluid in the chamber 208 of the drain apparatus 950 can be determined. Once the sound waves received by the ultrasonic receiver 912 indicate that level 906 of disinfectant fluid is at or near the top of the chamber 208, the drain apparatus valve 242 is closed to prevent any additional disinfectant fluid from entering the chamber 208 of the drain apparatus. In some implementations, once the sound waves received by the ultrasonic receiver 912 indicate that the liquid level 906 is at or near the top of the chamber 208, a signal is sent to close the water inlet valve 510 in order to prevent additional water from being added to the dialysis circuit 500 via the water inlet port 502 and stop the production of disinfectant fluid. After the disinfectant fluid has dwelled in the chamber 208 for the predetermined amount of time, the drain apparatus outlet valve 216 is opened and the drain apparatus pump 214 draws the disinfectant fluid out of the chamber 208 through outlet port 206 and the open drain apparatus outlet valve 216 to the drain line 112 via the outlet line 212. Any of various suitable ultrasonic transmitters and receivers can be used to detect fluid levels, such as an ultrasonic gap sensor.

Figure 14:
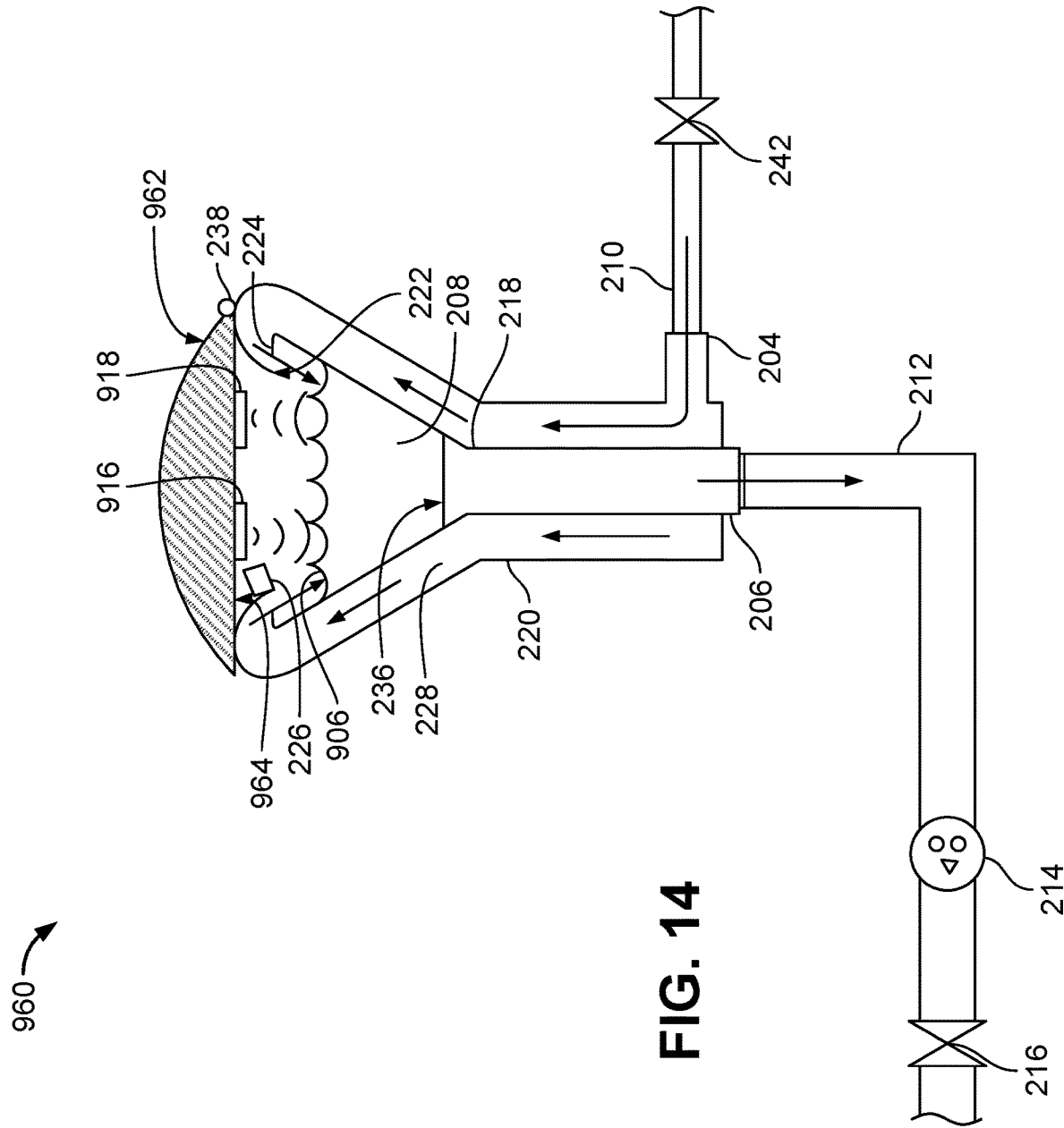

Referring to FIG. 14, in some implementations, the lid 962 of the drain apparatus 960 is not liquid-tight when in a closed position and the drain apparatus 962 includes a light transmitter 916 and light receiver 918 configured to detect the liquid level 906 inside the chamber 208 of the drain apparatus 960. In this arrangement, as disinfectant fluid enters the chamber 208, an equal amount of air contained in the chamber 208 exits around the non-liquid-tight lid 962. In some implementation, the lid 962 of the drain apparatus 960 includes vents or holes (such as holes 924 of FIG. 9). As shown in FIG. 14, the light transmitter 916 and light receiver 918 can be coupled to the inside surface 964 of lid 962 of the drain apparatus 960 facing towards the chamber 208 of the drain apparatus 960 when the lid 962 is in a closed position. During disinfection, drain apparatus outlet valve 216 is closed, lid 962 is closed over the chamber 208, disinfectant fluid is provided to the chamber 208 of the drain apparatus 960 via the inlet line 210, and the light transmitter 916 transmits light waves into the chamber 208. The light waves transmitted by light transmitter 916 bounce off the surface of liquid in the chamber 208 and are received by the light receiver 918. Based on the intensity of the light waves received by the light receiver 918, the level 906 of disinfectant fluid in the chamber 208 of the drain apparatus 960 can be determined. Once the light waves received by the light receiver 918 indicate that level 906 of disinfectant fluid is at or near the top of the chamber 208, the drain apparatus valve 242 is closed to prevent any additional disinfectant fluid from entering the chamber 208 of the drain apparatus. In some implementations, once the light waves received by the light receiver 918 indicate that the liquid level 906 is at or near the top of the chamber 208, a signal is sent to close the water inlet valve 510 in order to prevent additional water from being added to the dialysis circuit 500 via the water inlet port 502 and stop the production of disinfectant fluid. After the disinfectant fluid has dwelled in the chamber 208 for the predetermined amount of time, the drain apparatus outlet valve 216 is opened and the drain apparatus pump 214 draws the disinfectant fluid out of the chamber 208 through outlet port 206 and the open drain apparatus outlet valve 216 to the drain line 112 via the outlet line 212. Any of various suitable light transmitters and receivers can be used to detect fluid levels, such as an optical switch sensor.

Figure 15:
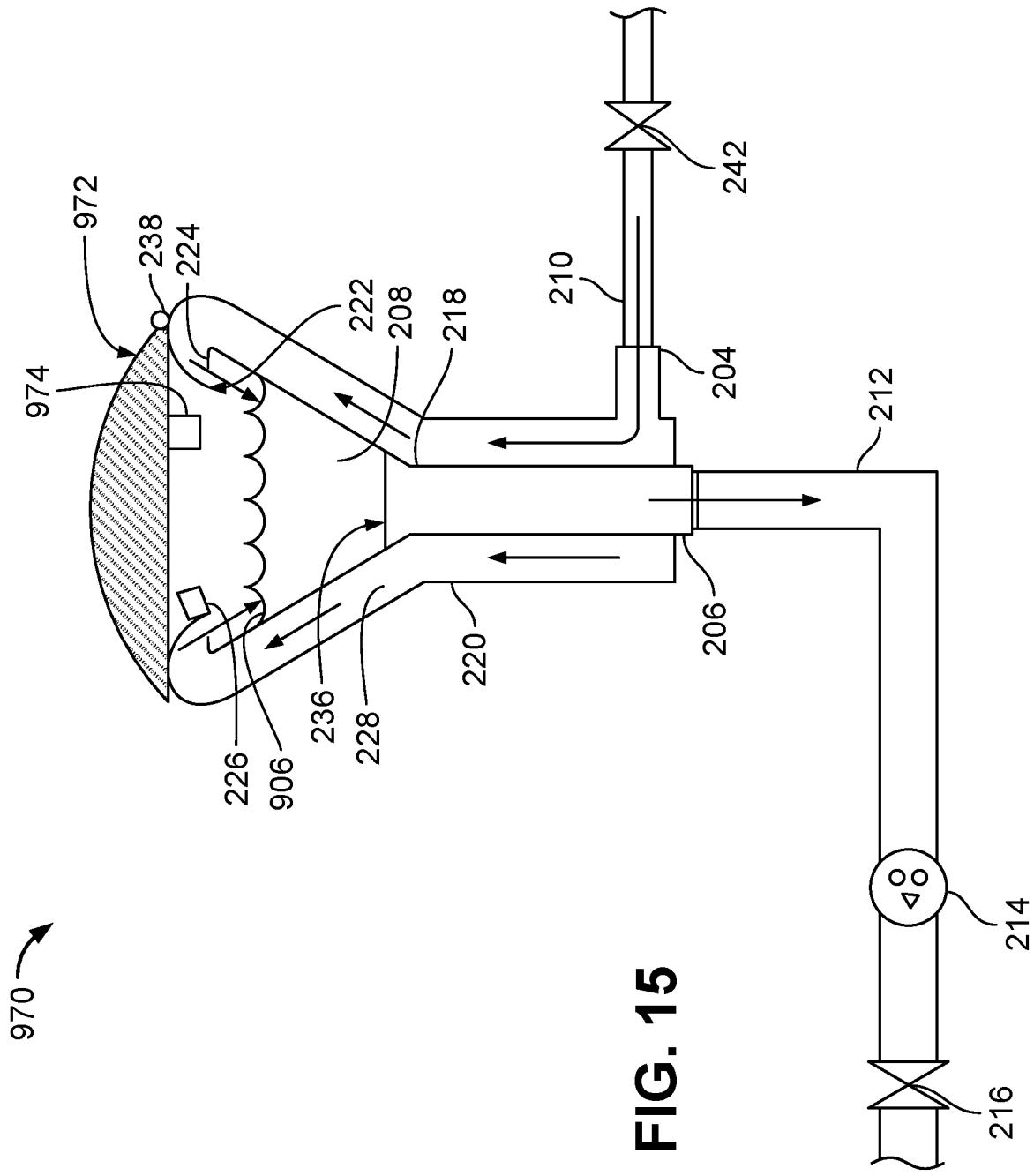

Referring to FIG. 15, in some implementations, the lid 972 of the drain apparatus 970 is not liquid-tight when in a closed position and the drain apparatus 970 includes a level sensor 974 coupled to the drain apparatus 970. Level sensor 974 is configured to detect the liquid level 906 inside the chamber 208 of the drain apparatus 970. For example, during disinfection, the level of disinfectant fluid in the chamber 208 of the drain apparatus 970 is monitored by the level sensor 974. During disinfection, drain apparatus outlet valve 216 is closed and disinfectant fluid is provided to the chamber 208 of the drain apparatus 970 via the inlet line 210. In this arrangement, as disinfectant fluid enters the chamber 208, an equal amount of air contained in the chamber 208 exits the chamber 208 around the non-liquid-tight lid 972. In some implementations, the lid 972 of the drain apparatus 970 includes vents or holes (such as holes 924 of FIG. 9). Once the level sensor 974 detects that level 906 of disinfectant fluid is at or near the top of the chamber 208, the drain apparatus valve 242 is closed to prevent any additional disinfectant fluid from entering the chamber 208 of the drain apparatus 970 and the disinfectant fluid is allowed to dwell in the chamber 208 for a predetermined amount of time. In some implementations, once the level sensor 974 detects that the liquid level 906 is at or near the top of the chamber 208 such that the chamber 208 is filled with fluid, a signal is sent to close the water inlet valve 510 in order to prevent additional water from being added to the dialysis circuit 500 via the water inlet port 502 and stop the production of disinfectant fluid. After the disinfectant fluid has dwelled in the chamber 208 for the predetermined amount of time, the drain apparatus outlet valve 216 is opened and the drain apparatus pump 214 draws the disinfectant fluid out of the chamber 208 through outlet port 206 and the open drain apparatus outlet valve 216 to the drain line 112 via the outlet line 212. Any of various suitable level sensors can be used, such as a level switch, a magnetic level switch, a magnetic float sensor, a pneumatic level sensor, an electrode level sensor, a conductivity level sensor, etc.

While the methods described above for disinfecting the drain apparatus 200 involve allowing the disinfectant fluid to dwell in the chamber 208 of the drain apparatus 200 for a predetermined amount of time, other techniques can alternatively or additionally be used. In some implementations, for example, once the chamber 208 of drain apparatus 200 is filled with disinfectant fluid (as determined using the methods above), the drain apparatus outlet valve 216 is opened to allow disinfectant fluid to flow through the outlet line 212 to the drain line 112, and additional disinfectant fluid is simultaneously provided to the chamber 208 via the inlet line 210. In some implementations, once the chamber 208 is filled with disinfectant fluid and the outlet valve 216 has been opened, the dialysate circuit 500 pumps disinfectant fluid to the chamber 208 via the inlet line 210 at a rate sufficient to maintain the disinfectant fluid level 906 in chamber 208 (i.e., keep the chamber filled with disinfectant fluid). This "continuous flow" method of draining and simultaneously filling of the chamber 208 of the drain apparatus 200 can be performed for a predetermined amount of time to ensure that the chamber 208 is properly disinfected. In some implementations, the disinfectant fluid continuously flows through and fills the chamber 208 for at least 10 minutes (e.g., at least 30 minutes, 10 to 60 minutes). In some examples, after the disinfectant fluid has been flowing and filling the chamber 208 for the predetermined amount of time, the drain apparatus inlet valve 242 is closed and the solution contained in the chamber 208 of the drain apparatus 200 exits the chamber 208 through drain apparatus outlet valve 216 via the outlet line 212 to the drain line 112.

Further, while the disinfectant fluid used to disinfect the dialysate circuit 500 and the drain apparatus 200 has been described as including a chemical disinfectant concentrate, the disinfectant fluid can alternatively be composed of hot water alone (i.e., without the addition of chemical disinfectant concentrate). In some examples, the disinfectant fluid is heated to a temperature of at least 80° C.

While the hydrophobic filter 232 of the drain apparatus 200 has been described as being arranged within the vent 230 of the drain apparatus, the hydrophobic filter 232 can alternatively be incorporated into the lid 952 of the drain apparatus 200. For example, the lid 952 can include an opening therethrough and the hydrophobic filter 232 can be arranged within the opening in the lid 202.

While the lid 202 has been described as being attached to the drain apparatus 200 using a hinge 238, the lid 202 can be attached to the drain apparatus 200 using alternative attachment mechanisms, such as clips, threads, an injection molded attachment, magnets, etc. In some examples, the lid 202 is attached to the drain apparatus 200 along a pivoting axis such that that lid 202 can be pivoted along to the axis to cover the drain apparatus 200. In some implementations, the lid 202 is pivoted about an axis by a stepper motor attached to the lid 202. In some embodiments, the lid 202 may be unattached from the drain apparatus 200 and can be placed on top of the apparatus 200 to seal the chamber 208, such as during disinfection of the chamber.

Figure 18:
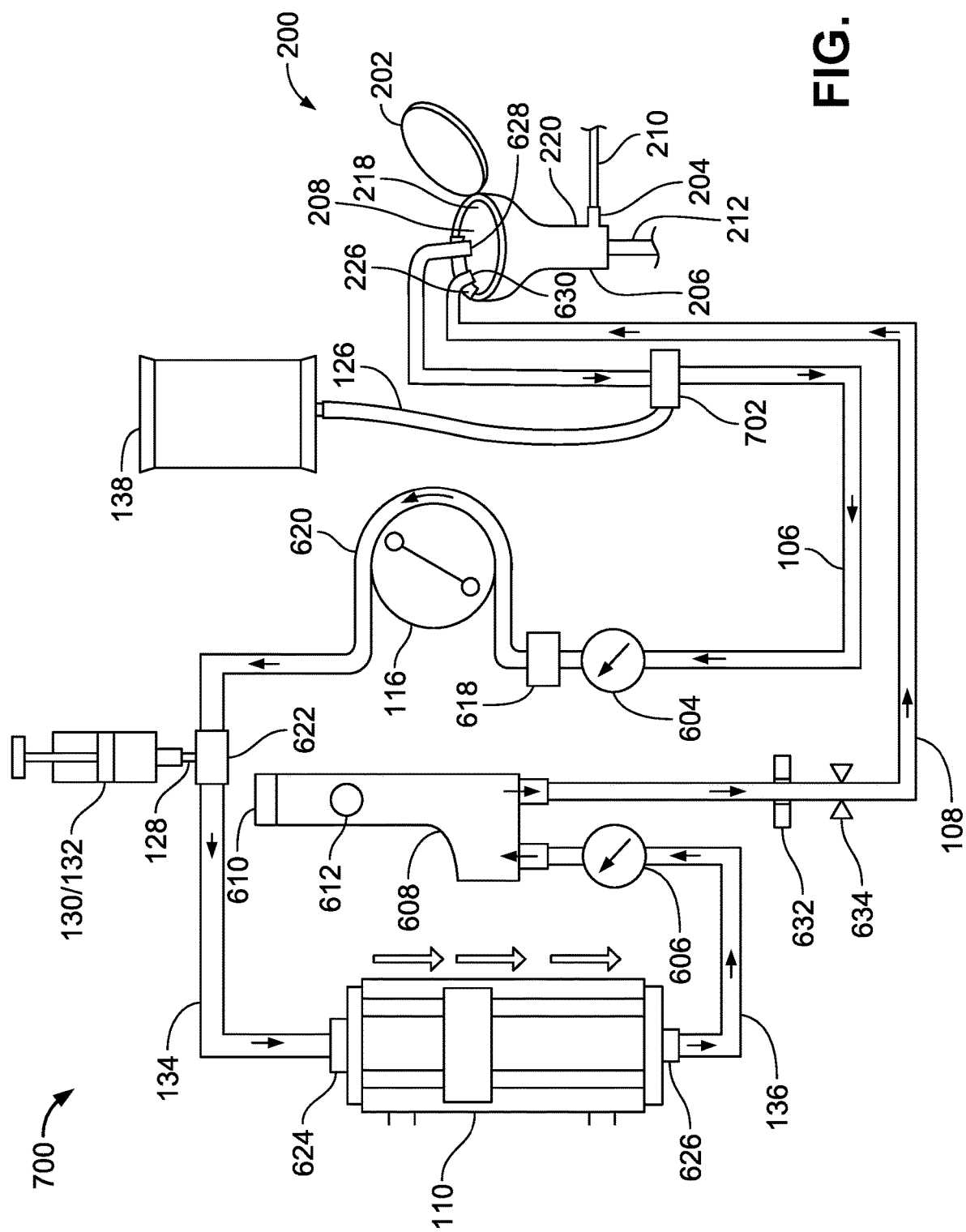
FIG. 18 is a schematic of a blood circuit and drain apparatus of the hemodialysis system of FIG. 1.

While the methods above involve attaching only the venous patient line 108 to the drain apparatus 200 during priming and following treatment, the arterial patient line 106 may additionally or alternatively be attached to the drain apparatus 200 to prime and flush the arterial patient line 106. For example, referring to FIG. 18, before priming the hemodialysis system 100, both the patient end 628 of the arterial patient line 106 and the patient end 630 of the venous patient line 108 can be attached to the drain apparatus 200 using the clip(s) 226 of the drain apparatus. A first end of the saline delivery line 126 can be attached to the saline bag 138 and a second end of the saline delivery line 126 can be attached to a port 702 on the arterial patient line 106. To begin priming the system 100, saline is introduced from the saline bag 138 through the saline delivery line 126 and through the port 702 on the arterial line 106. Saline is first provided to the portion of the arterial patient line 106 between the patient end 126 of the arterial patient line 106 and the port 702 on the arterial patient line 106.

Once the portion of the arterial patient line 106 between the patient end 126 of the arterial patient line 106 and the port 702 on the arterial patient line 106 is filled with saline, a clamp proximate the patient end 126 of the arterial patient line 106 is clamped. The blood pump 132 is then turned on to draw saline from the saline bag 138, through saline delivery line 126 and the port 702 on the arterial patient line 106, through a portion of the arterial patient line 106 between the port 702 on the arterial patient line 106 and the dialyzer 110. The saline flows into the dialyzer 110 via the dialyzer inlet line 134 and exits the dialyzer 110 via the dialyzer outlet line 136.

As the saline flows through the dialyzer outlet line 136 towards the air release device 608, the saline passes through the venous pressure sensor 606. Next, the saline flows through an entry port of the air release device 608 and fills the air release device 608. Once the air release device 608 is filled with saline, a clamp on the venous patient line 108 is removed and saline flows through the venous patient line 108 towards the patient end 630 of the venous patient line 108. Once the entire blood circuit 700 is filled with saline, any additional (e.g., excess) saline pumped through the blood component set 104 exits the patient end 630 of the venous patient line 108 and is captured by the chamber 208 of the drain apparatus 200. Once all air is out of the patient lines 106, 108 and the blood circuit 700 is filled with saline, a clamp is closed on the patient end 630 of the venous patient line 108. Once clamped, the patient ends 628, 630 of the patient lines 106, 108 are removed from the drain apparatus 200.

Similarly, in some implementations, both the arterial patient line 106 and the venous patient line 106 can be attached to the drain apparatus 200 to flush the patient lines 106, 108 following dialysis. For example, referring to FIG. 18, once a desired amount of the blood contained within the blood circuit 700 has been reinfused back to the patient 602, the patient lines 106, 108 are clamped, removed from the patient 602, and both the patient end 628 of the arterial patient line 106 and the patient end 630 of the venous patient line 108 are attached to the drain apparatus 200 using the clip(s) 226. A first end of the saline delivery line 126 can be attached to a saline bag 138 and a second end of the saline delivery line 126 can be attached to a port 702 on the arterial patient line 106. Saline is introduced from the saline bag 138 through the port 702 on the arterial line 106 via the saline delivery line 126.

Saline is first provided to the portion of the arterial patient line 106 between the patient end 126 of the arterial patient line 106 and the port 702 on the arterial patient line 106. The saline exits the patient end 628 of the arterial patient line 106 into the chamber 208 of the drain apparatus. Saline is continuously provided until all remaining patient fluids in the portion of the arterial patient line 106 between the patient end 126 of the arterial patient line 106 and the port 702 on the arterial patient line 106 have been flushed into the drain apparatus 200.

Once the portion of the arterial patient line 106 between the patient end 126 of the arterial patient line 106 and the port 702 on the arterial patient line 106 is flushed of patient fluids, a clamp proximate the patient end 126 of the arterial patient line 106 is clamped. The blood pump 132 is then turned on to draw saline from the saline bag 138 through the saline delivery line 126 and the port 702 on the arterial patient line 106 and circulate saline throughout all components of the blood circuit 700. After circulating through the blood circuit 700, the saline exits the patient end 630 of the venous patient line 108 and collects in the chamber 208 of the drain apparatus 200. The drain apparatus outlet valve 216 is open and the drain apparatus pump 214 is turned on to draw the saline collected from the venous patient line 108 by the drain apparatus 200 to the drain line 112 via the outlet line 212. Saline is continuously pumped through the blood circuit 700 until all remaining patient fluids have been flushed from the blood circuit 700 into the drain apparatus 200. In some cases, for example, saline is pumped through the blood circuit 700 until the saline bag 138 is empty.

While the drain apparatus 200 has been described as including a clip 226 to attach the venous patient line 108 to the drain apparatus 200, other mechanical attachment devices, such as clamps, ties, straps, hooks, latches, etc., can alternatively or additionally be used to attach the patient line(s) 106, 108 to the drain apparatus. In some implementations, the drain apparatus 200 includes two or more mechanical attachment devices.

Figure 17:
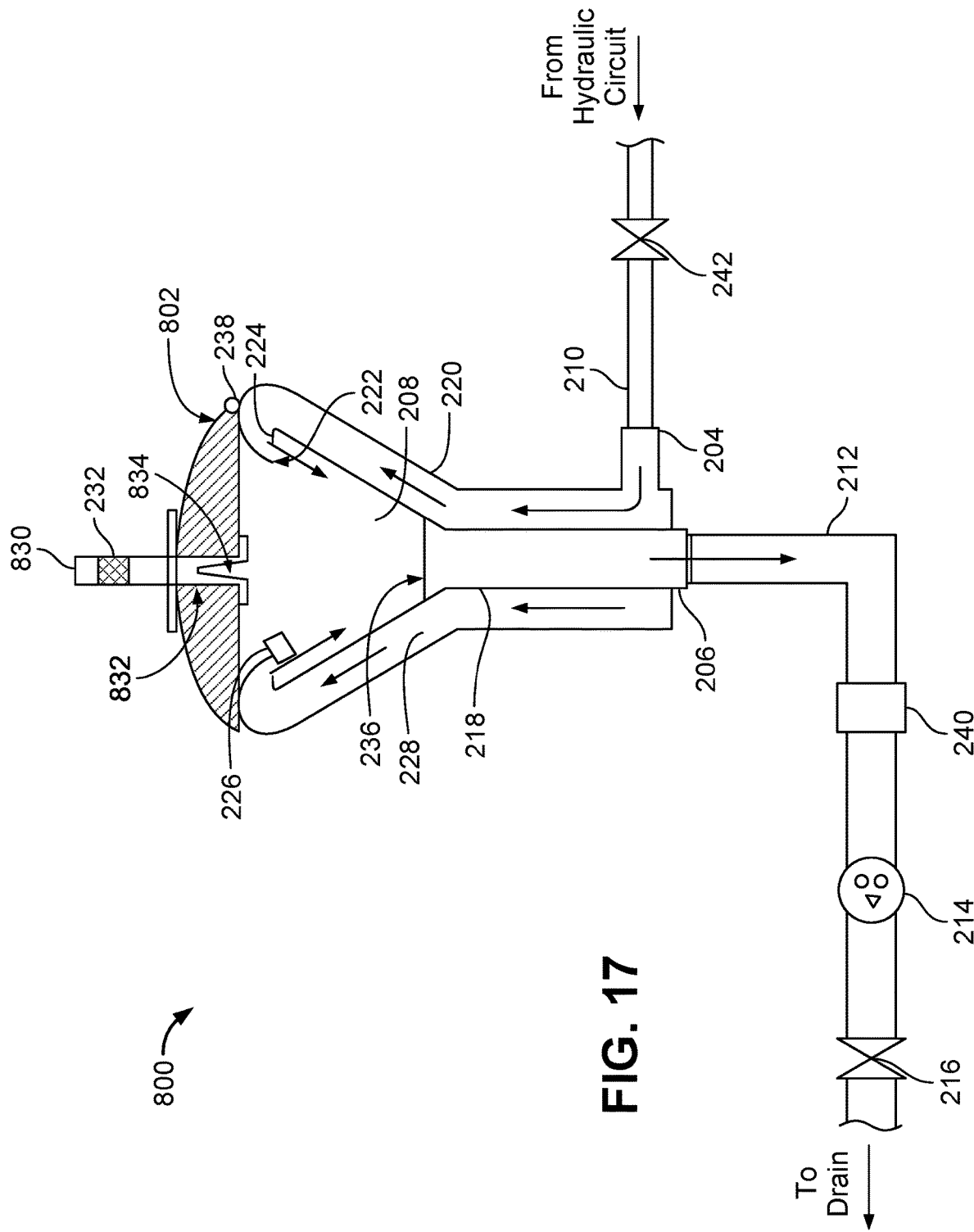
FIG. 17 is a cross-section view of an alternate drain apparatus for the hemodialysis system of FIG. 1.

While the drain apparatus 200 has been described as including a coupler 234 to attach the vent 230 to the lid 202 of the drain apparatus 200, in some examples the vent is coupled to the lid without a separate coupler. For example, as depicted in FIG. 17, drain apparatus 800 includes a vent 830 with a clip portion 832 that is configured to flex and fill an opening 834 in the lid 802 and couple the vent 830 to the lid 802. The clip portion 832 of the vent 830 is semi-rigid and compresses to fit into the opening 834 of the lid 802. In addition, once positioned within the opening 834, the clip portion 832 of the vent 830 expands to secure the vent 830 in place within the opening 834. In order to remove the vent 830 from the lid 802, a force is applied to the vent 830 and the diameter of the clip portion 832 of the vent 830 is compressed so that the clip portion 832 can slide out of the opening 834 of the lid 802. Once removed from the lid 802, the clip portion 832 of the vent 830 expands to its original, uncompressed diameter. In some examples, the vent 830 is replaced as part of periodic maintenance. In some implementations, a plurality of pores in hydrophobic filter 232 close in response to contact with water, and vent 830 is replaced following closure of the pores in the hydrophobic filter 232.

In some examples, a leak detection sensor is positioned below the drain apparatus 200 (e.g., proximate the outlet port 206 of the drain apparatus) to detect malfunctions in the drain apparatus 200 resulting in fluid leaks from the drain apparatus 200. The leak detection sensor can be communicably coupled to the drain apparatus inlet valve 242 and the drain apparatus inlet valve 242 can be automatically closed in response to the leak detection sensor detecting fluid leaking from the drain apparatus 200.

While the arterial pressure sensor 604 has been described as being arranged upstream of the blood pump 116 to measure a pre-pump arterial pressure, it can alternatively be positioned downstream of the blood pump 116 to measure a post-pump arterial pressure, or an additional arterial pressure sensor can be positioned downstream of the blood pump 116 to measure a post-pump arterial pressure.

While the methods above involve circulating saline through the patient lines 106, 108 and the blood circuit 600 to flush the patient lines 106, 108 and blood circuit of any remaining patient fluids, alternatively air may be pumped through the blood circuit 600 and patient lines 106, 108 to flush the patient lines 106, 108 and blood circuit 600 of any remaining patient fluids. For example, the arterial patient line 106 can be disconnected from the saline delivery line 126, and blood pump 116 can be used to draw air through the blood circuit 600 via the arterial patient line 106.

While the methods above involve using valves 538 through 552 to control flow of disinfectant fluid to alternate the flow of disinfectant fluid between the first chamber halves 558, 560 and second chamber halves 562, 564, alternatively all of the balancing device valves 538 through 552 can be opened during disinfection of the dialysate circuit 500. For example, during disinfection, all of valve 538 through 552 can be open such that disinfectant fluid flowing out of mixing chambers 534, 536 flows into all four chamber halves 558, 560, 562, 564 simultaneously.

While the methods above involve disinfectant fluid flowing into the second chamber halves 562, 564 of the balancing devices 554, 556 from the air separation chamber 593 and disinfectant fluid flowing out of the second chamber halves 562, 564 through valves 548, 552, alternatively valves 548 and 552 can remain closed during disinfection, such that as disinfectant fluid flows into first chamber half 558 of balancing devices 554, disinfectant fluid is simultaneously forced out of the second chamber half 562 of balancing device 554 and into the second chamber half 564 of balancing device 556. Similarly, in some implementations, as disinfectant fluid flows into first chamber half 560 of balancing devices 556, disinfectant fluid is simultaneously forced out of the second chamber half 564 of balancing device 556 and into the second chamber half 562 of balancing device 554.

A number of embodiments have been described. Nevertheless, it will be understood that various modifications may be made without departing from the spirit and scope of the disclosure. Accordingly, other embodiments are within the scope of the following claims.

What is claimed is:

1. A method comprising:

emptying contents of a blood line set of a dialysis system into a chamber of a drain apparatus of the dialysis system;

closing a lid of the drain apparatus to seal the chamber of the drain apparatus;

flowing a disinfectant fluid through an inlet line of the drain apparatus from a dialysis machine of the dialysis system to the drain apparatus to at least partially fill the chamber of the drain apparatus with the disinfectant fluid; and flowing the disinfectant fluid through an outlet line of the drain apparatus from the drain apparatus to a drain line of the dialysis machine.

2. The method of claim 1, wherein emptying contents of a blood line set of a dialysis system into a chamber of a drain apparatus of the dialysis system comprises:

connecting a patient line of the blood line set to the drain apparatus of the dialysis machine following performance of dialysis on a patient;

flowing a saline solution through the patient line of the blood line set into the drain apparatus to flush remaining fluid in the blood line set into the drain apparatus; and disconnecting the patient line of the blood line set from the drain apparatus.

3. The method of claim 1, further comprising stopping flow of the disinfectant fluid upon receiving a signal from a sensor coupled to the drain apparatus indicating that the chamber of the drain apparatus is filled with disinfectant solution.

4. The method of claim 1, wherein the disinfectant fluid dwells in the chamber of the drain apparatus for a predetermined amount of time.

5. The method of claim 1, wherein flowing the disinfectant fluid through the outlet line of the drain apparatus from the drain apparatus to the drain line of the dialysis machine comprises opening a valve coupled to the outlet line of the drain apparatus.

6. The method of claim 1, wherein flowing the disinfectant fluid through the outlet line of the drain apparatus from the drain apparatus to the drain line of the dialysis machine comprises pumping the disinfectant fluid in the chamber of the drain apparatus to the drain line using a pump coupled to the outlet line of the drain apparatus.

7. The method of claim 1, wherein flowing the disinfectant fluid through the outlet line of the drain apparatus from the drain apparatus to the drain line of the dialysis machine comprises using negative pressure generated by a flow pump of the dialysis machine to pump the disinfectant fluid in the chamber of the drain apparatus to the drain line.

8. The method of claim 1, wherein the disinfectant fluid comprises a chemical disinfectant.

9. The method of claim 1, wherein the disinfectant fluid is hot water.

10. The method of claim 1, wherein flowing the disinfectant fluid through the inlet line of the drain apparatus from the dialysis machine to the drain apparatus to at least partially fill the chamber of the drain apparatus comprises flowing the disinfectant fluid into the chamber at a rate sufficient to maintain a predetermined level of fluid in the chamber for a predetermined amount of time.

* * * * *